US007049062B1

(12) United States Patent
Clark et al.

(10) Patent No.: US 7,049,062 B1
(45) Date of Patent: May 23, 2006

(54) ASSAY FOR METHYLATION IN THE GST-PI GENE

(75) Inventors: Susan J. Clark, New South Wales (AU); Douglas S. Millar, New South Wales (AU); Peter L. Molloy, New South Wales (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 0 days.

(21) Appl. No.: 09/673,448

(22) PCT Filed: Apr. 23, 1999

(86) PCT No.: PCT/AU99/00306

§ 371 (c)(1),
(2), (4) Date: Nov. 27, 2000

(87) PCT Pub. No.: WO99/55905

PCT Pub. Date: Nov. 4, 1999

(30) Foreign Application Priority Data

Apr. 23, 1998 (AU) ........................... PP3129

(51) Int. Cl.
*C12Q 1/68* (2006.01)
(52) U.S. Cl. .................. 435/6; 435/91.1; 435/91.2; 536/23.1; 536/24.3
(58) Field of Classification Search .............. 435/6, 435/91.2; 536/23.1, 24.3
See application file for complete search history.

(56) References Cited

U.S. PATENT DOCUMENTS 5,552,277 A * 9/1996 Nelson et al. .................. 435/6
5,786,146 A * 7/1998 Herman et al. ................. 435/6

FOREIGN PATENT DOCUMENTS

| AU | 31341/95 | 2/1996 |
| WO | WO 96/02674 | 2/1996 |
| WO | WO 97/46705 | 12/1997 |

OTHER PUBLICATIONS

Morrow et al. "Homo sapiens glutathone S-transferase pi (GSTPi) gene". Genbank Accession No. M24485, Dec. 1994.*
Virmani et al. "Aberrant Methylation during cervical carcinogenesis" Clinical Cancer Research. vol. 7, pp. 584-589, Mar. 2001.*
Melki et al. "Concurrent DNA Hypermethylation of multiple genes in acute myeloid leukemia" Cancer Research, vol. 59, pp. 3730-3740, Aug. 1999.*
Bakker et al. "Methyl-CpG binding domain protein 2 repressess transcription from hypermethylated pi-class glutatione S-transferase gene promoters in HCC" J. of Biological Chemistry. vol. 277, No. 25, pp. 22573-22580, Jun. 2002.*
Tchou et al. "CpG island methylation near the GST-Pi promoter in HCC-the role of GSTpi expression in human hepatocarcinogenesis" Hepatology. vol. 28, No. 4, Part. 2, Supp. abstract #37, Oct. 1998.*
Lee et al, *Cancer Epidemiology, Biomarkers and Prevention*, 6:443-450 (1997).
Brooks et al, *Cancer Epidemiology, Biomarkers and Prevention*, 7:531-536 (1998).
Jhaveri et al, *Gene*, 210(1):1-7 (1998).
Esteller et al, *Cancer Research*, 58:4515-4518 (1998).
Lee et al, *Proc. Natl. Acad. Sci., USA*, 91:11733-11737 (1994).
Millar et al, *Oncogene*, 18(6):1313-1324 (1999).
Frommer et al, *Proc. Natl. Acad. Sci., USA*, 89:1827-1831 (1992).
Lee et al, *Proceedings of the American Assoc. for Cancer Res. Annual Meeting*, 36(0):538 (1995).
Lin et al, *J. of Urology*, 157(No. 4 Suppl.):343 (1997).
Tascilar et al, *J. of Urology*, 155(No. 5 Suppl.):625A (1996).
Yang et al, *Proceedings of the American Assoc. for Cancer Res. Annual Meeting*, 38(0):182 (1997).
Herman et al, *Proc. Of the Nat. Acad. of Sci. of USA, Natl. Acad. of Sci.*, 93(1):9821-9826 (1996).
Gonzalgo et al, *Cancer Research*, 57:5336-5347 (1997).
Malloy et al, *Today's Life Science*, 11(5):34-35 (1999).
Liu et al, *Cancer Res.*, 57(17):3629-3634 (1997).
Latza et al, *J. Clin. Pathol.*, 43(3):213-219 (1990).
Barany et al, *Proc. Natl. Acad. Sci.*, 88:189-193 (1991).
Holland et al., *Proc. Natl.Acad. Sci., USA*, 88:7276-7280 (1991).
Gruenbaum et al, *Nature*, 292(5826):860-862 (1981).
Holliday et al., *Science*, 187(4173):226-232 (1975).
Riggs, *Cytogenet. Cell Genet.*, 14(1):9-25 (1975).
Graessmann et al, *In DNA Methylation*: Molecular Biology and Biological Significance, Saluz Ed., (Birkhauser Verlag, Basel, Switzerland), pp. 404-424 (1993).
Stirzaker et al, *Cancer Res.*, 57(11):2229-2237 (1997).

(Continued)

*Primary Examiner*—Jeanine A. Goldberg
(74) *Attorney, Agent, or Firm*—Sughrue Mion, PLLC

(57) ABSTRACT

A diagnostic or prognostic assay is disclosed for a disease of condition characterized by abnormal methylation of cytosine at side or sites within the glutathione-S-transferase (GST) Pi gene and/or its regulatory flanking sequences (e.g., prostate cancer and liver cancer). The assay comprises: (i) isolating DNA from said subject, and (ii) determining (e.g., by selective PCR amplification) the presence of abnormal methylation of cytosine at a site or sites within the GST-Pi gene and/or its regulatory flanking sequences.

33 Claims, 17 Drawing Sheets

OTHER PUBLICATIONS

Figure 1:
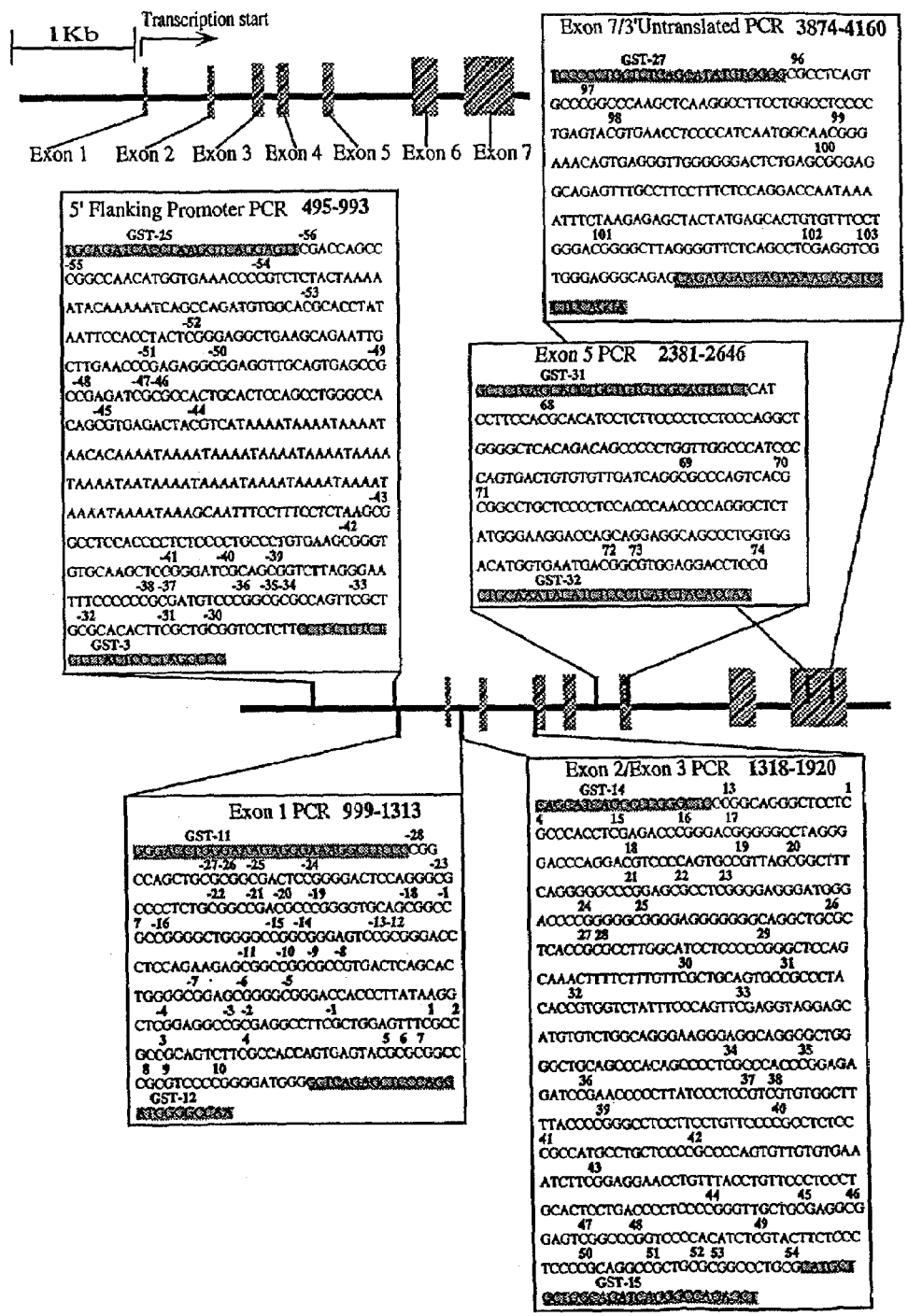

Tremblay et al, *Molecular and Cellular Biology*, 17(8):4322-4329 (1997).

Shapiro et al, *J. of Biological Chemistry*, 248(11):4060-4064 (1973).

Wang et al, *Nucleic Acids Res.*, 8(20):4777-4790 (1980).

Lee et al, *Cancer Epidermology, Biomarkers & Prevention*, 6:443-450 (1997).

Herman et al, *Proc. Natl. Acad. Sci., USA*, 93:9821-9826 (1996).

Frommer et al, *Proc. Natl. Acad. Sci., USA*, 89(1827-1831 (1992).

Lee et al, *Proc. Natl. Acad. Sci., USA*, 91:11733-11737 (1994).

Clark et al, *Biotechnuques*, 21(1):126-133 (1996).

Clark et al, *Nat. Genet.*, 10(1):20-27 (1995).

* cited by examiner

Figure 2        Upstream Region of Differential Methylation in Prostate Cancer

```
                                                              -43                                            -42
ATAAAATAAA ATAAAATAAA ATAAAGCAAT TTCCTTTCCT CTAAGCGGCC TCCACCCCTC TCCCCTGCCC TGTGAAGCGG  -355
ATAAAATAAA ATAAAATAAA ATAAAGTAAT TTTTTTTTTT TTAAGTGGTT TTTATTTTTT TTTTTTGTTT TGTGAAGTGG  B-U
ATAAAATAAA ATAAAATAAA ATAAAGTAAT TTTTTTTTTT TTAAGCGGTT TTTATTTTTT TTTTTTGTTT TGTGAAGCGG  B-M

GTA-GC (p)
           -41       -40                                              -38 -37    -36-35-34     -32    -33
GTGTGCAAGC TCCGGGATCG CAGCGGTCTT AGGGAATTTC CCCCCGCGAT GTCCCGGCGC GCCAGTTCGC TGCGCACACT  -275
GTGTGTAAGT TTTGGGATTG TAGTGGTTTT AGGGAATTTT TTTTTTGTGAT GTTTTGGTGT GTTAGTTTGT TGTGTATATT  B-U
GTGTTAAGT TTCGGGATCG TAGCGGTTTT AGGGAATTTT TTTTCGCGAT GTTCGGCGC GTTAGTTCGT TGCGTATATT  B-M

CGPS-5   YGGTTTT  AGGGAATTTT TTTTCGC>CGPS-6 YGGYGY GTTAGTTYGT TGYGTATATT
                    CGPS-11  GGGAATTTT  TTTTCGGCGAT GTTTYGGCGC>

-29                                                 -28
-31  -30
TCGCTGCGCT CCTCTTCCTG CTGTCTGTTT ACTCCCCTAGG CCCCGCTGGG GACCTGGGAA AGAGGGAAAG GCTTCCCCGG  -195
TTGTTGTGT  TTTTTTTTTG TTGTTTGTTT ATTTTTTAGG  TTTTGTTGGG GATTGGGAA AGAGGGAAA GTTTTTTTGG  B-U
TCGTTGCGT  TTTTTTTTTG TTGTTTGTTT ATTTTTTAGG  TTTCGTTGGG GATTGGGAA AGAGGGAAA GTTTTTTCGG  B-M

TC>

-23                      -22 -21 -20 -19                    -18 -17 -16
-27-26-25  -24
CCAGCTGCGC GGGACTCCAG GGCGCCCCTC TGCGGCCGAC GCCCGGGGTG CAGCGGCCGC CGGGGCTGGG  -115
TTAGTTGTGT GGTGTTTTTG GGTGTTTTTT TGTGGTTGAT GTTTGGGGTG TAGTGGTTGT TGGGGTTGGG  B-U
TTAGTTGCGC GGCGATTTAG GGCGTTTTTT TGCGGTCGAC GTTCGGGGTG TAGCGGTTCGT CGGGGTTGGG  B-M

<GCG CCRCTAAAARC CCCTAAAATC CCRC CGPS-7  < GCTG CAARCCCCAC ATCRCCARCA RCCCCA CGPS-8
<G CCCGCTAAAGC CCCTAAAATC CCRCAAAAA CGPS-12                   <GCCARCA GCCCAACCC
```

Figure 2 (Continued)

```
-15 -14      -13 -12                           -11 -10  -9  -8                        -7      -6      -5
GCCGGCGGGA GTCCGCGGGA CCCTCCAGAA GAGCGGCCGG CGCCGTGACT CAGCACTGGG GCGGAGCGGG GCGGGACCAC -35
GTTGGTGGGA GTTGTGGGA TTTTTAGAA GAGTGGTTGG TGTTGTGATT TAGTATTGGG GTGGAGTGGG GTGGGATTAT B-U
GTCGGCGGGA GTTCGCGGGA TTTTTAGAA GAGCGGTCGG CGTCGTGATT TAGTATTGGG GCGGAGCGGG GCGGGATTAT B-M

<GCCGCCCT CAARCRCCCT AAAAAATCTT CTC   CGPS-9
 CAGCCRCCCT CAA  CGPS-13

-4      -3      -2                    -1  >                  1   2   3      4                 5   6   7
CCTTATAAGG CTCGGAGGCC GCGAGGCCTT CGCTGGAGTT TCGCCGCCGC AGTCTTCGCC ACCAGTGAGT ACGGCGGCC +46
TTTTATAAGG TTTGGAGGTT GTGAGGTTTT TGTTGGAGTT TTGTTGTTGT AGTTTTTTGTT ATTAGTGAGT ATGTGTGGTT B-U
TTTTATAAGG TTCGGAGGTC GCGAGGTTTT CGTTGGAGTT TCGTCGTCGT AGTTTTTCGTT ATTAGTGAGT ACGGCGGGTT B-M

CGPS-1    C  GCGAGGTTTT CGTTGGAGTT TCGTCGTC>  CGPS-2   CGTT ATTAGTGAGT ACGCGCGGTT 8 9    10
CGCGTCCCCG GGGATGGGGC TCAGAGCTCC CAGCATGGGG CCAA +90
TGTGTTTTTG GGGATGGGGT TTAGAGTTTT TAGTATGGGG TTAA B-U
CGCGTTTTCG GGGATGGGGT TTAGAGTTTT TAGTATGGGG TTAA B-M

C>
```

Figure 3A  Methylation Status of Individual Sites in the GST-Pi Gene

| site | LN | Du | PC3 | PC3 M | PC3 MM | 2AN | BN CN | 2AC | BC | CC | DC | XC | WC | Pr |
|---|---|---|---|---|---|---|---|---|---|---|---|---|---|---|
| | | | | | | | | 4+4 | 3+3 | 2+3 | 2+2 | 3+4 | 3+3 | |
| -28 | ++++ | . | + | | | . | . | . | | | | | | . |
| -27 | ++++ | . | + | ++ | ++ | . | . | . | ++ | + | ++ | ++++ | ++ | . |
| -26 | ++++ | . | + | ++ | ++ | . | . | . | + | + | ++ | ++++ | + | . |
| -25 | ++++ | . | + | ++ | ++ | . | . | . | ++ | ++ | ++ | ++++ | ++ | . |
| -24 | ++++ | . | ++ | ++ | ++ | . | . | . | ++ | ++ | ++ | ++++ | ++ | . |
| -23 | ++++ | . | ++ | + | + | . | . | . | ++ | ++ | ++ | ++++ | ++ | . |
| -22 | ++++ | . | + | + | + | . | . | . | + | ++ | ++ | | ++ | . |
| -21 | ++++ | . | . | . | . | . | . | . | ++ | ++ | ++ | . | + | . |
| -20 | ++++ | . | . | . | . | . | . | . | + | ++ | ++ | ++ | ++ | . |
| -19 | ++++ | . | ++ | + | ++ | . | . | . | ++ | ++ | ++ | ++++ | ++ | . |
| -18 | ++++ | . | + | + | ++ | . | . | . | + | ++ | ++ | ++++ | ++ | . |
| -17 | ++++ | . | + | + | ++ | . | . | . | + | ++ | ++ | ++++ | + | . |
| -16 | ++++ | . | + | + | + | . | . | . | +B | ++B | ++ | ++ | + | . |
| -15 | ++++ | . | . | ++ | ++ | . | . | . | B | B | B | . | + | . |
| -14 | ++++ | . | + | ++ | ++ | . | . | . | B | B | B | ++ | + | . |
| -13 | ++++ | . | + | ++ | ++ | . | . | . | ++ | ++ | ++ | ++++ | ++ | . |
| -12 | ++++ | . | ++ | ++ | ++ | . | . | . | ++ | ++ | ++ | ++++ | ++ | . |
| -11 | ++++ | . | ++ | + | ++ | . | . | . | ++ | + | ++ | ++++ | ++ | . |
| -10 | ++++ | . | ++ | ++ | ++ | . | . | . | ++ | ++ | ++ | ++++ | +++ | . |
| -9 | ++++ | . | ++ | ++ | ++ | . | . | . | ++ | ++ | +++ | ++++ | +++ | . |
| -8 | ++++ | . | ++ | ++ | ++ | . | . | . | ++ | ++ | +++ | ++++ | +++ | . |
| -7 | ++++ | . | ++ | ++ | ++ | . | . | . | ++ | ++ | +++ | ++++ | +++ | . |
| -6 | ++++ | . | ++ | ++ | ++ | . | . | . | ++ | ++ | +++ | ++++ | +++ | . |
| -5 | ++++ | . | ++ | ++ | ++ | . | . | . | ++ | ++ | +++ | ++++ | +++ | . |
| -4 | ++++ | . | ++ | ++ | ++ | . | . | . | ++ | ++ | ++ | ++++ | +++ | . |
| -3 | ++++ | . | ++ | ++ | ++ | . | . | . | ++ | ++ | ++ | ++++ | ++ | . |
| -2 | ++++ | . | ++ | ++ | B | . | . | . | +++ | ++ | ++ | ++++ | ++ | . |
| -1 | ++++ | . | ++ | + | B | . | . | . | ++ | ++ | ++ | ++++ | ++ | . |

Figure 3A (cont'd)

Figure 3A (cont'd)

Figure 3B:
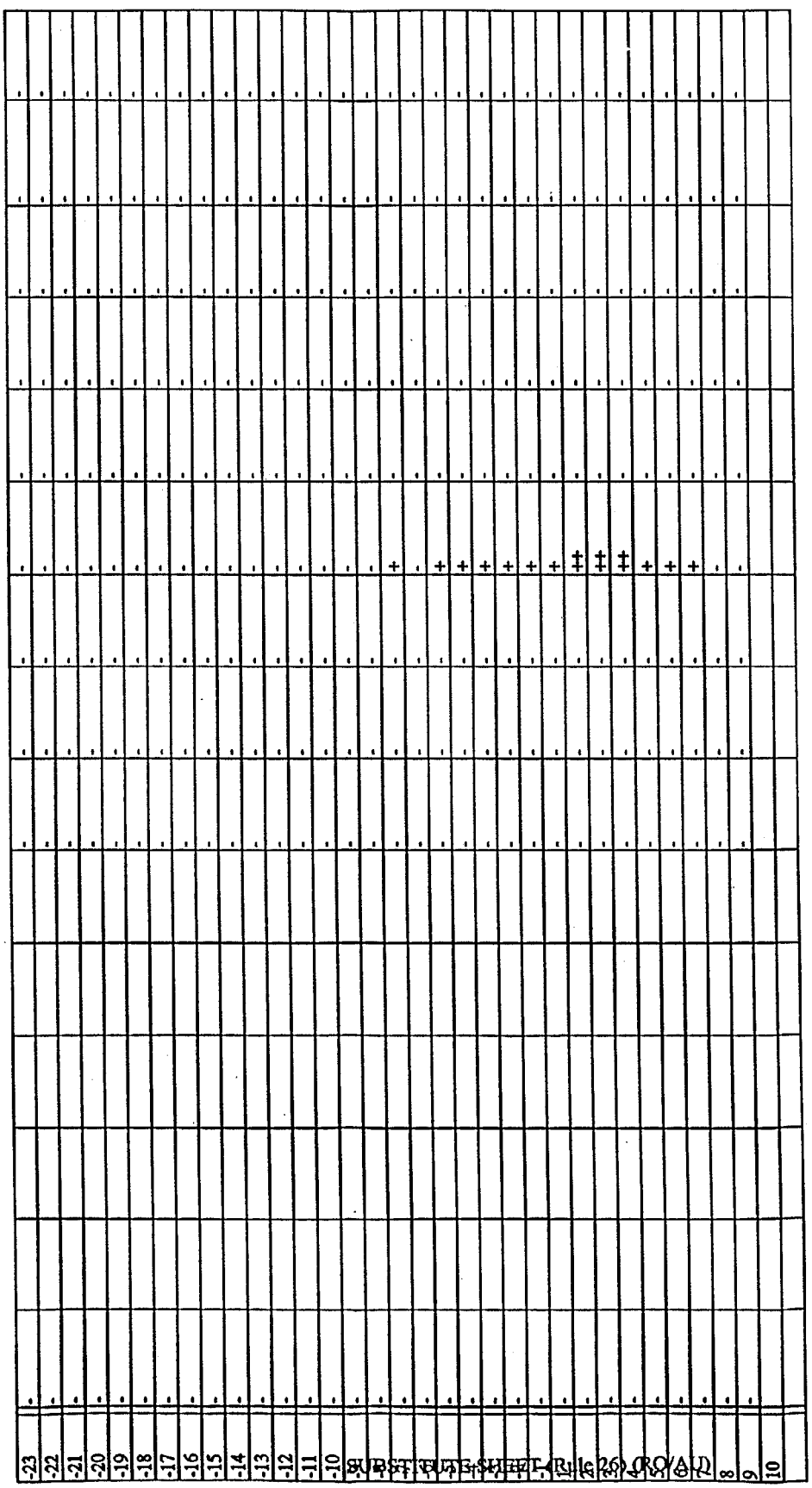

Figure 3B Methylation Status of Individual Sites in the GST-Pi Gene

| Site | Normal Prostate (15) | PC-3 (10) | LNCaP (7) | BC (9) | CC (4) | DC (10) | Blood (13) | Brain (6) | Spleen (6) | Liver (6) | Smooth muscle (6) | Lung (5) | Bone marrow (5) | Pancreas (6) | Heart (3) |
|---|---|---|---|---|---|---|---|---|---|---|---|---|---|---|---|
| -56 | +++ | . | +++ | ++ | ++ | ++ | +++ | +++ | +++ | +++ | +++ | ++ | +++ | ++ | +++ |
| -55 | +++ | ++ | +++ | ++ | + | ++ | +++ | +++ | +++ | ++ | +++ | ++ | +++ | ++ | +++ |
| -54 | ++ | + | +++ | ++ | + | ++ | +++ | +++ | +++ | +++ | +++ | +++ | +++ | ++ | +++ |
| -53 | +++ | . | +++ | +++ | . | + | +++ | + | ++ | + | . | + | ++ | ++ | +++ |
| -52 | ++ | + | +++ | + | ++ | ++ | +++ | ++ | ++ | . | ++ | +++ | +++ | ++ | +++ |
| -51 | + | . | +++ | ++ | ++ | +++ | +++ | +++ | +++ | ++ | + | +++ | +++ | ++ | +++ |
| -50 | ++ | ++ | +++ | + | ++ B | +++ | +++ | +++ | +++ | + | . | . | ++ | ++ | . |
| -49 | ++ | + | +++ | ++ | ++ | +++ | +++ | ++ | +++ | + | . | . | + | + | + |
| -48 | + | ++ | ++ | + | +++ | +++ | +++ | + | ++ | + | . | ++ | ++ | ++ | + |
| -47 | ++ | +++ | +++ | + | ++ | +++ | ++ | ++ | ++ | + | . | +++ | ++ | ++ | . |
| -46 | ++ | + | +++ | + | ++ | +++ | +++ | ++ | ++ | . | . | . | . | . | ++ |
| -45 | . | . | ++ | . | ++ | +++ | +++ | + | ++ | . | . | . | . | . | . |
| -44 | . | . | +++ | +++ | +++ | +++ | . | . | . | . | . | . | . | . | . |
| -43 | . | . | +++ | +++ | +++ | +++ | . | . | . | . | . | . | . | . | . |
| -42 | . | . | +++ | +++ | +++ | +++ | . | + | . | . | . | + | . | . | . |
| -41 | . | . | +++ | +++ | +++ | ++++ | . | . | . | . | . | . | . | . | . |
| -40 | . | . | +++ | +++ | ++++ | ++++ | . | . | . | . | . | . | . | . | . |
| -39 | . | . | +++ | (+++)p | ++++ | (+++)p | . | . | . | . | . | . | . | . | . |
| -38 | . | . | +++ | +++ | +++ | ++ | . | . | . | . | . | . | . | . | . |
| -37 | . | . | B | +++ | ++ | +++ | . | . | . | . | . | . | . | . | . |
| -36 | . | . | B | ++ | ++ | +++ | . | . | . | . | . | . | . | . | . |
| -35 | . | . | B | ++ | ++ | ++ | . | . | . | . | . | . | . | . | . |
| -34 | . | . | . | . | . | . | . | . | . | . | . | . | . | . | . |
| -33 | p | . | . | . | . | . | . | . | . | . | . | . | . | . | . |
| -32 | . | . | . | . | . | . | . | . | . | . | . | . | . | . | . |
| -31 | . | . | . | . | . | . | . | . | . | . | . | . | . | . | . |
| -30 | . | . | . | . | . | . | . | . | . | . | . | . | . | . | . |
| -28 | . | . | . | . | . | . | . | . | . | . | . | . | . | . | . |
| -27 | . | . | . | . | . | . | . | . | . | . | . | . | . | . | . |
| -26 | . | . | . | . | . | . | . | . | . | . | . | . | . | . | . |
| -25 | . | . | . | . | . | . | . | . | . | . | . | . | . | . | . |
| -24 | . | . | . | . | . | . | . | . | . | . | . | . | . | . | . |

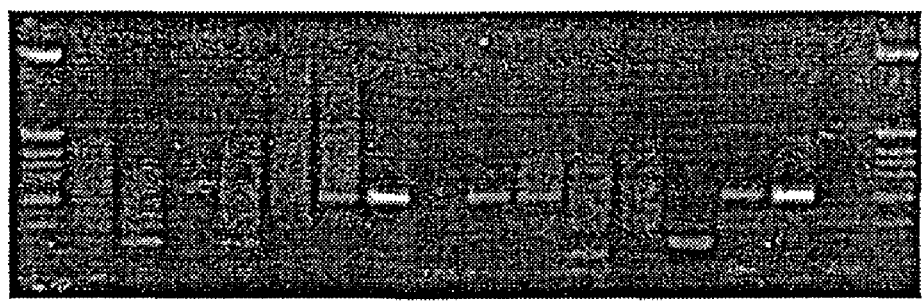
FIGURE 4A

Sample Number
1 2 3 4 5 6 7 8 9 10
M n c n c n c n c n c n c n c n c n c n c + −

| Sample | Tissue | Gleason | % Methylation Non CG rich PCR |
|---|---|---|---|
| 1 | Normal | N/A | − |
|   | Cancer | 3+3 | ++++ |
| 2 | Normal | N/A | − |
|   | Cancer | 3+5 | ++ |
| 3 | Normal | N/A | − |
|   | Cancer | 3+3 | ++ |
| 4 | Normal | N/A | − |
|   | Cancer | 3+5 | − |
| 5 | Normal | N/A | − |
|   | Cancer | 2+2 | ++ |
| 6 | Normal | N/A | − |
|   | Cancer | 3+3 | − |
| 7 | Normal | N/A | − |
|   | Cancer | 2+3 | ++ |
| 8 | Normal | N/A | − |
|   | Cancer | 3+3 | ++ |
| 9 | Normal | N/A | − |
|   | Cancer | 2+3 | ++++ |
| 10 | Normal | N/A | − |
|   | Cancer | ? | ++ |

A
B
C
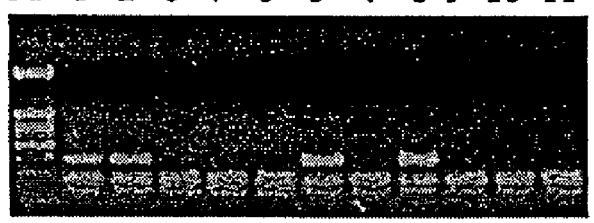
FIGURE 4C

Liver Cancer Tissue DNA extracts

ASSAY FOR METHYLATION IN THE GST-PI GENE

This application is a 371 of PCT/AU99/00306 filed Apr. 23, 1999.

FIELD OF THE INVENTION

This invention relates to an assay for diagnosis or prognosis of a disease or condition characterised by abnormal methylation of cytosine at a site or sites within the glutathione-S-transferase (GST) Pi gene and/or its regulatory flanking sequences. In one particular application, the invention provides an assay for the diagnosis or prognosis of prostate cancer.

BACKGROUND OF THE INVENTION

DNA Methylation in Mammalian Genomes

The only established post-synthetic modification of DNA in higher animal and plant genomes is methylation of the 5' position of cytosine. The proportion of cytosines which are methylated can vary from a few percent in some animal genomes (1) to 30% in some plant genomes (2). Much of this methylation is found at CpG sites where the symmetrically positioned cytosines on each strand are methylated. In plant genomes, similar symmetrical methylation of cytosines at CpNpG (where N can be any base) is also common (3). Such sites of methylation have also been identified at low frequency in mammalian DNA (4).

Methylation patterns are heritable as the methylase enzyme recognises as a substrate, sites where a CpG dinucleotide is methylated on one strand but the corresponding C on the other strand is unmethylated, and proceeds to methylate it (5, 6). Fully unmethylated sites do not normally act as substrates for the enzyme and hence remain unmethylated through successive cell divisions. Thus, in the absence of errors or specific intervening events, the methylase enzyme enables the stable heritability of methylation patterns.

Extensive studies of gene expression in vertebrates have shown a strong correlation between methylation of regulatory regions of genes and their lack of expression (7). Most of such studies have examined only a limited number of restriction enzyme sites using enzymes which fail to cut if their target sites are methylated. A far more limited number have been examined at all cytosine bases using genomic sequencing methods (8, 9).

Bisulphite Conversion Of DNA

Treatment of single-stranded DNA with high concentrations of bisulphite followed by alkali leads to the selective deamination of cytosine, converting it to uracil (10, 11). By contrast, 5-methyl cytosines (5meC) are resistant to this chemical deamination. When bisulphite-treated DNA is copied by DNA polymerases, the uracils are read as if they were thymines and an adenine nucleotide incorporated, while 5meC is still read as a cytosine (a G being incorporated opposite). Thus, after a region of sequence is amplified by polymerase chain reaction (PCR), cytosines in the sequence which were methylated in the original DNA will be read as cytosines while unmethylated cytosines will be read as thymines (12, 13).

PCR Amplification of Methylated and Unmethylated DNA

In order to amplify bisulphite-treated DNA, primers are designed to anneal to the sequence produced after bisulphite treatment of the DNA. Since cytosines are converted to uracils, the base in the annealing primer will be an adenine rather than a guanine for the non-converted cytosine. Similarly, for the other primer of the pair, thymines replace cytosines. To permit quantification of levels of methylation in the target DNA, primers are normally chosen to avoid sites which may or may not be methylated (particularly CpG sites) and so may contain either a 5meC or a uracil after bisulphite treatment. Use of such non-selective primers allows both methylated and unmethylated DNAs to be amplified by PCR providing for quantification of the level of methylation in the starting DNA population. The PCR-amplified DNA can be cut with an informative restriction enzyme, can be sequenced directly to provide an average measure of the proportion of methylation at any position or molecules may be cloned and sequenced (each clone will be derived from amplification of an individual strand in the initial DNA). Such studies have indicated that, while a population of molecules may conform to an overall pattern of methylation, not all molecules will be identical and methylation may be found on only a fraction of molecules at some sites (13, 16).

Selective Amplification of Methylated DNA

Recently Herman et al. (14) described a variation of the bisulphite sequencing procedure to make it selective for the amplification of only methylated DNA. In this work, PCR primers were used which were designed to discriminate between the sequences produced after bisulphite-treatment of methylated and non-methylated target DNAs. Thus, cytosines which formed part of a CpG site would not be bisulphite converted and would remain as cytosines in the methylated DNA but would be converted to uracils in the unmethylated target DNA. Primers utilising these differences were designed and used for the amplification of methylated DNA sequences from four tumour suppressor genes, p16, p15, E-cadherin and von Hippel-Lindau.

Methylation of the GLUTATHIONE-S-TRANSFERASE Pi Gene in Prostate Cancer

Lee et al. (15) (U.S. Pat. No. 5,552,277 and International Patent Application No PCT/US95/09050) demonstrated that expression of the glutathione-S-transferase (GST) Pi gene is lost in nearly all cases of prostate cancer. They further showed that in twenty cases examined, using Southern blotting, that this loss of expression was accompanied by methylation at a specific restriction enzyme site (BssHII) in the promoter region of the gene. This methylation was not seen in normal prostate tissue or in a number of other normal tissues examined. In examining a prostate cancer cell line in which the GST-Pi gene is inactive, they also identified methylation at two other restriction enzyme sites, NotI and SacII in the promoter region of the gene. Digestion of cell line DNAs with the enzymes MspI and HpaII, indicated that the correlation of DNA methylation with lack of expression was not maintained for these sites which were largely located downstream of the transcription start site. The nature of the data makes it difficult to reach conclusions on the methylation status of individual MspI/HpaII sites. However, Lee et al. (18) were able to show that following HpaII digestion (which will cut at all unmethylated HpaII sites), a region of DNA containing twelve HpaII recognition sites could be amplified by PCR from tumour DNA, but not from normal prostate or leukocyte DNA. This indicates that some DNA molecules in prostate cancer are methylated at all these HpaII sites, while DNAs from normal prostate and leukocyte DNA must contain at least one of these sites unmethylated (as a single cut will render the region incapable of being amplified by PCR).

The present inventors have identified and developed an alternative method for detecting sites of methylation present in DNA from prostate cancer tissue but not present in DNA from normal tissue. The method relies on selective amplification of a target region of the GST-Pi gene but does not require prior restriction with an informative restriction enzyme.

DISCLOSURE OF THE INVENTION

Thus, in a first aspect, the present invention provides a diagnostic or prognostic assay for a disease or condition in a subject, said disease or condition characterised by abnormal methylation of cytosine at a site or sites within the glutathione-S-transferase (GST) Pi gene and/or its regulatory flanking sequences, wherein said assay comprises the steps of;
  (i) isolating DNA from said subject,
  (ii) exposing said isolated DNA to reactants and conditions for the amplification of a target region of the GST-Pi gene and/or its regulatory flanking sequences which includes a site or sites at which abnormal cytosine methylation characteristic of the disease or condition occurs, the amplification being selective in that it only amplifies the target region if the said site or sites at which abnormal cytosine methylation occurs is/are methylated, and
  (iii) determining the presence of amplified DNA, wherein the amplifying step (ii) is used to amplify a target region of the GST-Pi gene and/or its regulatory flanking sequences defined by (and inclusive of) CpG sites −43 to +55.

Since the amplification is designed to only amplify the target region if the said site or sites at which abnormal cytosine methylation (i.e. as compared to the corresponding site or sites of DNA from subjects without the disease or condition being assayed) occurs is/are methylated, the presence of amplified DNA will be indicative of the disease or condition in the subject from which the isolated DNA has been obtained. The assay thereby provides a means for diagnosing or prognosing the disease or condition in a subject.

The step of isolating DNA may be conducted in accordance with standard protocols. The DNA may be isolated from any suitable body sample, such as cells from tissue (fresh or fixed samples), blood (including serum and plasma), semen, urine, lymph or bone marrow. For some types of body samples, particularly fluid samples such as blood, semen, urine and lymph, it may be preferred to firstly subject the sample to a process to enrich the concentration of a certain cell type (e.g. prostate cells). One suitable process for enrichment involves the separation of required cells through the use of cell-specific antibodies coupled to magnetic beads and a magnetic cell separation device.

Prior to the amplifying step, the isolated DNA is preferably treated such that unmethylated cytosines are converted to uracil or another nucleotide capable of forming a base pair with adenine while methylated cytosines are unchanged or are converted to a nucleotide capable of forming a base pair with guanine. This treatment permits the design of primers which enable the selective amplification of the target region if the said site or sites at which abnormal cytosine methylation occurs is/are methylated.

Preferably, following treatment and amplification of the isolated DNA, a test is performed to verify that unmethylated cytosines have been efficiently converted to uracil or another nucleotide capable of forming a base pair with adenine, and that methylated cystosines have remained unchanged or efficiently converted to another nucleotide capable of forming a base pair with guanine.

Preferably, the treatment of the isolated DNA involves reacting the isolated DNA with bisulphite in accordance with standard protocols. As will be clear from the above discussion of bisulphite treatment, unmethylated cytosines will be converted to uracil whereas methylated cytosines will be unchanged. Verification that unmethylated cytosines have been converted to uracil and that methylated cystosines have remained unchanged may be achieved by;
  (i) restricting an aliquot of the treated and amplified DNA with a suitable restriction enzyme(s) which recognise a restriction site(s) generated by or resistant to the bisulphite treatment, and
  (ii) assessing the restriction fragment pattern by electrophoresis. Alternatively, verification may be achieved by differential hybridisation using specific oligonucleotides targeted to regions of the treated DNA where unmethylated cytosines would have been converted to uracil and methylated cytosines would have remained unchanged.

The amplifying step may involve polymerase chain reaction (PCR) amplification, ligase chain reaction amplification (20) and others (21).

Preferably, the amplifying step is conducted in accordance with standard protocols for PCR amplification, in which case, the reactants will typically be suitable primers, dNTPs and a thermostable DNA polymerase, and the conditions will be cycles of varying temperatures and durations to effect alternating denaturation of strand duplexes, annealing of primers (e.g. under high stringency conditions) and subsequent DNA synthesis.

To achieve selective PCR amplification with bisulphite-treated DNA, primers and conditions may be used to discriminate between a target region including a site or sites of abnormal cytosine methylation and a target region where there is no site or sites of abnormal cytosine methylation. Thus, for amplification only of a target region where the said site or sites at which abnormal cytosine methylation occurs is/are methylated, the primers used to anneal to the bisulphite-treated DNA (i.e. reverse primers) will include a guanine nucleotide(s) at a site(s) at which it will form a base pair with a methylated cytosine(s). Such primers will form a mismatch if the target region in the isolated DNA has unmethylated cytosine nucleotide(s) (which would have been converted to uracil by the bisulphite treatment) at the site or sites at which abnormal cytosine methylation occurs. The primers used for annealing to the opposite strand (i.e. the forward primers) will include a cytosine nucleotide(s) at any site(s) corresponding to site(s) of methylated cytosine in the bisulphite-treated DNA.

Preferably, the primers used for the PCR amplification are of 12 to 30 nucleotides in length and are designed to anneal to a sequence within the target region that includes two to four cytosine nucleotides that are abnormally methylated in the DNA of a subject with the disease or condition being assayed. In addition, the primers preferably include a terminal nucleotide that will form a base pair with a cytosine nucleotide (reverse primer), or the guanine nucleotide opposite (forward primer), that is abnormally methylated in the DNA of a subject with the disease or condition being assayed.

The step of amplifying is used to amplify a target region within the GST-Pi gene and/or its regulatory flanking sequences. The regulatory flanking sequences may be regarded as the flanking sequences 5' and 3' of the GST-Pi gene which include the elements that regulate, either alone or in combination with another like element, expression of the GST-Pi gene.

In particular, the step of amplifying is used to amplify a target region within the region of the GST-Pi gene and its regulatory flanking sequences defined by (and inclusive of) CpG sites −43 to +55 (wherein the numbering of the CpG sites is relative to the transcription start site). The numbering and position of CpG sites is shown in FIG. 1.

The step of determining the presence of amplified DNA may be conducted in accordance with standard protocols. One convenient method involves visualisation of a band(s) corresponding to amplified DNA, following gel electrophoresis.

Preferably, the disease or condition to be assayed is selected from cancers, especially hormone dependent cancers such as prostate cancer, breast cancer and cervical cancer, and liver cancer.

For the diagnosis or prognosis of prostate cancer, the step of amplifying preferably amplifies a target region within the region of the GST-Pi gene and its regulatory flanking sequences defined by (and inclusive of) CpG sites −43 to +53, more preferably, −43 to +10. However, within these target regions it is believed that there are CpG sites which show variability in methylation status in prostate cancer or are methylated in other tissues. Thus, for the target region defined by (and inclusive of) CpG sites −43 to +10, it is preferred that the primers used for amplification be designed so as to minimise (i.e. by use of redundant primers or by avoidance of the sites) the influence of CpG sites −36, −32, −23, −20, −19, −14 and a polymorphic region covering site −33. Further, for DNA isolated from cells other than from prostate tissue (e.g. blood), it is preferred that the primers used be designated to amplify a target region that does not include the region of the GST-Pi gene and its regulatory flanking sequences defined by (and inclusive of) CpG sites −7 to +7, or, more preferably, −13 to +8, since this may lead to false positives. Further preferred target regions, therefore, are within the region of the GST-Pi gene and its regulatory flanking sequences defined by (and inclusive of) CpG sites −43 to −14, −43 to −8, +9 to +53 and +1 to +53.

Suitable primer pairs for the diagnosis or prognosis of prostate cancer, include those consisting of a forward and reverse primer selected from each of the following groups:

Forward Primers (i.e. anneal to the 5' end of the target region)
CGCGAGGTTTTCGTTGGAGTTTCGTCGTC (SEQ ID NO: 1)
CGTTATTAGTGAGTACGCGCGGTTC (SEQ ID NO: 2)
YGGTTTTAGGGAATTTTTTTTCGC (SEQ ID NO: 3)
YGGYGYGTTAGTTYGTTGYGTATATTTC (SEQ ID NO: 4)
GGGAATTTTTTTTCGCGATGTTTYGGCGC (SEQ ID NO: 5)
TTTTTAGGGGGTTYGGAGCGTTTC (SEQ ID NO: 6)
GGTAGGTTGYGTTTATCGC (SEQ ID NO: 7)
Reverse Primers (i.e. anneal to the extension of the forward primer)
TCCCATCCCTCCCCGAAACGCTCCG (SEQ ID NO: 8)
GAAACGCTCCGAACCCCCTAAAAACCGCTAACG (SEQ ID NO: 9)
CRCCCTAAAATCCCCRAAATCRCCGCG (SEQ ID NO: 10)
ACCCCRACRACCRCTACACCCCRAACGTCG (SEQ ID NO: 11)
CTCTTCTAAAAAATCCCRCRAACTCCCGCCG (SEQ ID NO: 12)
AAAACRCCCTAAAATCCCCGAAATCGCCG (SEQ ID NO: 13)
AACTCCCRCCGACCCCAACCCCGACGACCG (SEQ ID NO: 14)
AAAAATTCRAATCTCTCCGAATAAACG (SEQ ID NO: 15)
AAAAACCRAAATAAAAACCACACGACG (SEQ ID NO: 16)

wherein Y is C, T or, preferably, a mixture thereof, and R is A, G or, preferably, a mixture thereof.

For the diagnosis or prognosis of liver cancer, the step of amplifying preferably amplifies a target region within the region of the GST-Pi gene and its regulatory flanking sequences defined by (and inclusive of) CpG sites −43 to −14 and/or +9 to +53. However, within these target regions it is believed that there are CpG sites which show variability in methylation status in liver cancer or are methylated in other tissues. Thus, for the target region defined by (and inclusive of) CpG sites −43 to −14, it is preferred that the primers used for amplification be designed so as to minimise (i.e. by use of redundant primers or by avoidance of the sites) the influence of CpG sites −36, −32, −23, −20, −19, −14 and a polymorphic region covering site −33.

It will be appreciated by persons skilled in the art, that a site or sites of abnormal cytosine methylation within the above identified target regions of the GST-Pi gene and/or its regulatory flanking sequences, could be detected for the purposes of diagnosing or prognosing a disease or condition (particularly, prostate cancer and/or liver cancer) by methods which do not involve selective amplification. For instance, oligonucleotide/polynucleotide probes could be designed for use in hybridisation studies (e.g. Southern blotting) with bisulphite-treated DNA which, under appropriate conditions of stringency, selectively hybridise only to DNA which includes a site or sites of abnormal methylation of cytosine(s). Alternatively, an appropriately selected informative restriction enzyme(s) could be used to produce restriction fragment patterns that distinguish between DNA which does and does not include a site or sites of abnormal methylation of cytosine(s).

Thus, in a second aspect, the present invention provides a diagnostic or prognostic assay for a disease or condition in a subject said disease or condition characterised by abnormal methylation of cytosine at a site or sites within the glutathione-S-transferase (GST) Pi gene and/or its regulatory flanking sequences, wherein said assay comprises the steps of;

(i) isolating DNA from said subject, and
(ii) determining the presence of abnormal methylation of cytosine at a site or sites within the region of the GST-Pi gene and/or its regulatory flanking sequences defined by (and inclusive of) CpG sites −43 to +55.

The step of isolating DNA may be conducted as described above in relation to the assay of the first aspect.

Preferably, the region of the GST-Pi gene and its regulatory flanking sequences within which the presence of methylated cytosine(s) at a site or sites is determined is selected from the regions defined by (and inclusive of) CpG sites −43 to +53, −43 to +10, −43 to −14, +9 to +53 and +1 to +53. However, within these regions, it is preferred that certain sites (namely, CpG sites, −36, −33, −32, −23, −20, −19, and −14) be avoided as the site or sites at which, for the purpose of the assay, the presence of abnormal methylation of cytosine is determined.

Where the determination step is to involve selective hybridisation of oligonucleotide/polynucleotide/peptide-nucleic acid (PNA) probes, prior to the determination step, the isolated DNA is preferably treated (e.g. with bisulphite) such that unmethylated cytosines are converted to uracil or another nucleotide capable of forming a base pair with adenine while methylated cytosines are unchanged or are converted to a nucleotide capable of forming a base pair with guanine. This treatment permits the design of probes which allow for selective hybridisation to a target region including a site or sites of abnormal methylation of cytosine.

In a third aspect, the present invention provides a primer or probe (sequence shown in the 5' to 3' direction) comprising a nucleotide sequence selected from the group consisting of:
CGCGAGGTTTTCGTTGGAGTTTCGTCGTC (SEQ ID NO: 1)
CGTTATTAGTGAGTACGCGCGGTTC (SEQ ID NO: 2)
YGGTTTTAGGGAATTTTTTTTCGC (SEQ ID NO: 3)
YGGYGYGTTAGTTYGTTGYGTATATTTC (SEQ ID NO: 4)
GGGAATTTTTTTTCGCGATGTTTYGGCGC (SEQ ID NO: 5)
TTTTTAGGGGGTTYGGAGCGTTTC (SEQ ID NO: 6)
GGTAGGTTGYGTTTATCGC (SEQ ID NO: 7)
AAAAATTCRAATCTCTCCGAATAAACG (SEQ ID NO: 8)
AAAAACCRAAATAAAAACCACACGACG (SEQ ID NO: 9)
TCCCATCCCTCCCCGAAACGCTCCG (SEQ ID NO: 10)
GAAACGCTCCGAACCCCCTAAAAACCGCTAACG (SEQ ID NO: 11)
CRCCCTAAAATCCCCRAAATCRCCGCG (SEQ ID NO: 12)
ACCCCRACRACCRCTACACCCCRAACGTCG (SEQ ID NO: 13)
CTCTTCTAAAAAATCCCRCRAACTCCCGCCG (SEQ ID NO: 14)
AAAACRCCCTAAAATCCCCGAAATCGCCG (SEQ ID NO: 15)
AACTCCCRCCGACCCCAACCCCGACGACCG, (SEQ ID NO: 16)
wherein Y is C, T or, preferably, a mixture thereof, and R is A, G or, preferably, a mixture thereof.

The terms "comprise", "comprises" and "comprising" as used throughout the specification are intended to refer to the inclusion of a stated component, feature or step or group of components, features or steps with or without the inclusion of a further component, feature or step or group of components, features or steps.

The invention will now be further described with reference to the accompanying figures and following, non-limiting examples.

BRIEF DESCRIPTION OF THE ACCOMPANYING FIGURES

FIG. 1 shows the organisation and nucleotide sequence of human GST-Pi gene. CpG sites are numbered relative to the transcription start site. Nucleotide Sequence numbering is according to the GST-Pi gene sequence of Genbank Accession No. M24485 (SEQ ID NO:60).

FIG. 2 shows the region of the GST-Pi gene exhibiting differential methylation in prostate cancer. The figure further shows the sequence and derivation of primers for the upstream region (from CpG site −43 to +10) and the common polymorphism encompassing CpG site −33 (shown above the sequence (p)). Underneath the GST-Pi sequence is shown the sequence of the derived strand after conversion of cytosines to uracil. The derived strand is shown either assuming all CpGs are methylated (B-M) or un-methylated (B-U). Below this is shown specific primers designed to selectively amplify the methylated sequence.

FIG. 3 shows the methylation status of each CpG site in isolated DNAs;

A—for the core promoter region through to the 3' end of the GST-Pi gene for the LNCaP (LN) cell line, DU145 (DU) cell line, PC3 cell line, PC3-M cell line and PC3-MM cell line, for DNA isolated from normal tissue samples from prostate cancer patients (2AN, BN and CN), for prostate tumour tissue (BC, CC, DC, XC, WC and 2AC) and for normal prostate tissue (Pr) from a person without prostate cancer;

B—for the core promoter region and upstream sequences of the GST-Pi gene from normal prostate tissue (from a person without prostate cancer), from three prostate cancer samples (BC, CC and DC) and for a number of other normal tissues. Patients B and D were polymorphic at CpG site −33 and the level of methylation indicated in the brackets reflects methylation of the allele which contains the CpG. For CpG sites −28 to +10, the level of metylation was determined by direct sequence analysis of the population of PCR molecules (17). For the upstream CpG sites, −56 to −30, PCR products were cloned and a number of individual clones sequenced (number indicated in brackets below the sample name). For normal tissues the level of methylation at each site was determined as the fraction of all clones containing a C at that position. For the cancer samples BC, CC and DC, the level of methylation shown is that among the clones which showed DNA metlhylation in the region from CpG site −43 to −30 (about half of the clones in each case).

In both A and B, a blank box indicates that the site was not assayed, and a "B" indicates that the status of the site could not be determined (e.g. because of a sequence blockage or it was beyond the range of the sequencing run). The level of methylation detected at each site is shown, none (−), up to 25% (+), 26–50% (++), 51–75% (+++) and 76–100% (++++). The Gleason Grade of tumour samples is also shown.

FIG. 4 provides the results of amplification of bisulphite treated DNAs from a variety of tissues;

A—panel A (region covering the transcription start site) used CGPS-1 and 3 as outer primers and CGPS-2 and 4 as inner primers, Panel B used the outer primer pair CGPS-5 and 8 which encompass the region from CpG site −39 to −16 for first round amplification, followed by a second round of amplification with the CGPS-6 and 7 primers, amplifying a 140 bp fragment covering CpG sites −36 to −23. The lanes are 1. Brain, 2. Lung, 3. Skeletal muscle, 4. Spleen, 5. Pancreas. 6. "Normal" Prostate Aged 85 y.o., 7. "Normal" Prostate Aged 62 y.o., 8. Heart. 9. Bone Marrow, 10. Blood-1, 11. Blood-2, 12. Blood-3, 13. Liver-1, 14. Liver-2.

B—used the same primer pairs as that of the amplification shown in FIG. 4A Panel B, with DNA from 10 prostate cancer tissue samples (c) and matched normal (n) tissue samples from the same prostates (a positive control (+) LNCaP DNA and a negative control (−) is also shown). Underneath, is the Gleason grade and the level of methylation of samples seen with non-selective primers.

C—used the same primer pairs as that of the amplification shown in FIG. 4A Panel B, with DNA from a range of healthy tissues, blood from prostate cancer patients and various cell lines. The lanes are: Panel A 1–10 blood samples from prostate cancer patients during radical prostacectomy; Panel B 1. normal prostate-1, 2. normal prostate-2, 3. normal prostate-3, 4. normal prostate-4, 5. normal prostate-5, 6. HPV transformed prostate cell line, 7. blood from prostate patient PA (PSA=1000), 8. blood from prostate patient PB (PSA=56), 9. blood from prostate patient PC(PSA=18); and Panel $C_1$. LNCaP cell line, 2. Du145 cell line, 3. PC-3 cell line, 4. PC-3M cell line, 5. PC-3MM cell line, 6. Hela cell line, 7. leukemic DNA, 8. HepG2 cell line, 9. human liver DNA, 10. white blood cells, 11. MRC-5 cell line.

Figure 5:
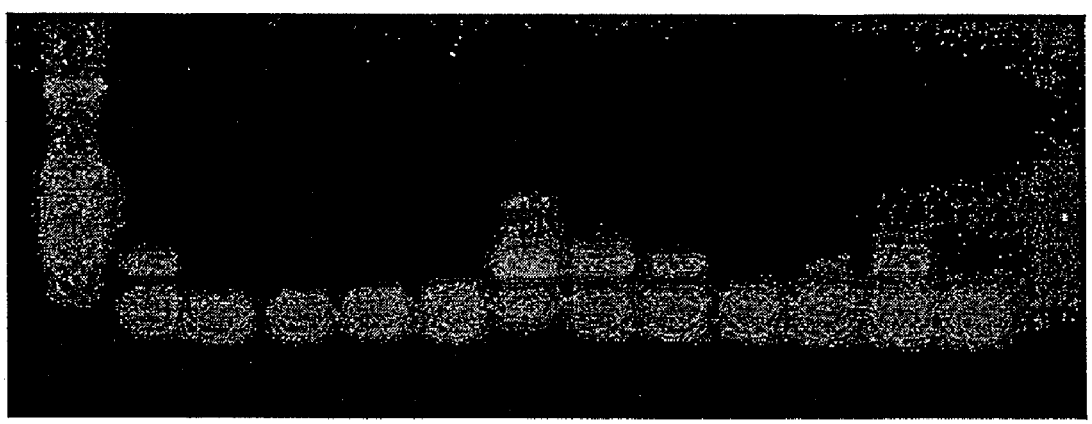

FIG. 5 provides the results of amplification of bisulphite treated DNAs from seminal fluid of prostate cancer patients (c) and from men with no diagnosed prostate cancer (n), using the outer primer pair CGPS-5 and 8 and CGPS-6 and 7 as the inner primer pair. The lanes are L. LNCaP cell line (positive control), D. DU145 cell line, P. PC-3 cell line (negative controls), and M. molecular weight markers.

Figure 6:
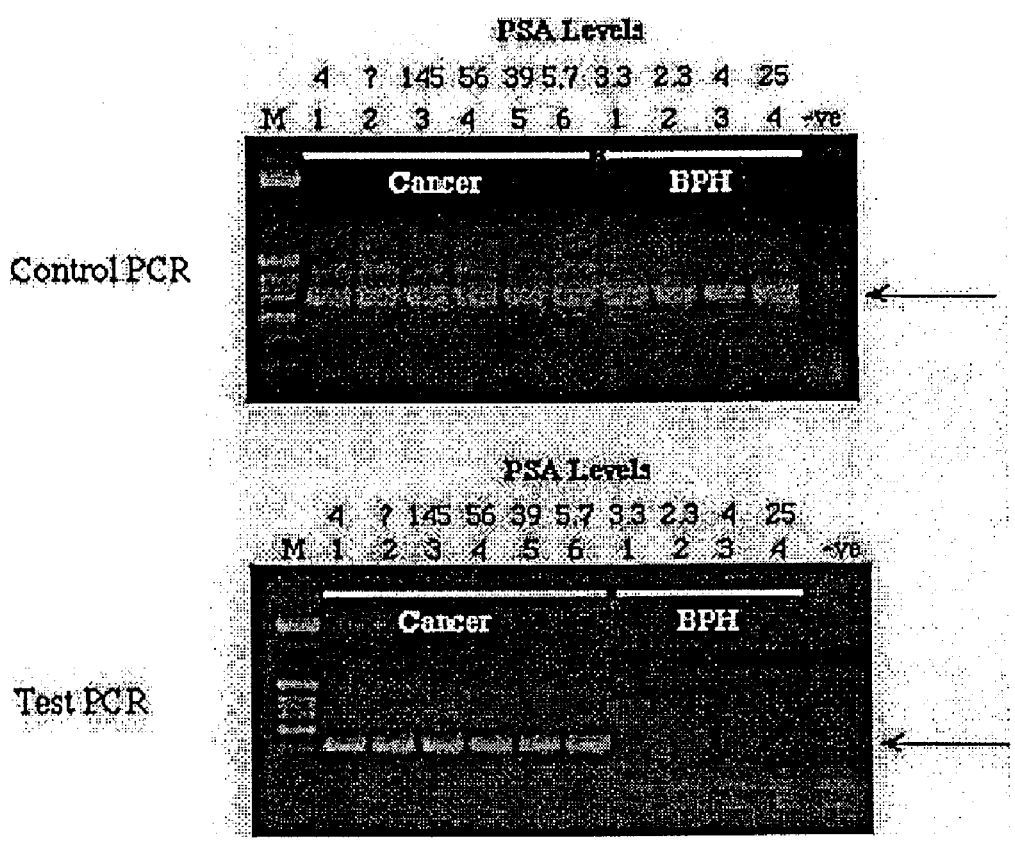

FIG. 6 shows the results of amplification of bisulphite treated DNAs, wherein the DNA has been isolated from prostate tissue slides that had been identified as either cancerous or diseased with benign hyperplasia (BPH). Selective PCR amplification was conducted using the outer primer pair CGPS-5 and 8 and the inner primer pair CGPS-11 and 12.

FIG. 7 shows the results of amplification of bisulphite treated DNAs, wherein the DNA has been isolated from prostate cancer cells enriched from blood samples using magnetic beads coated with an anti-epithelial antibody. Different numbers of LNCaP prostate cancer cells were added to the blood samples (7A) or blood with added LNCaP cells stored for different times at 4° C. or room temperature prior to DNA isolation.

Figure 8:
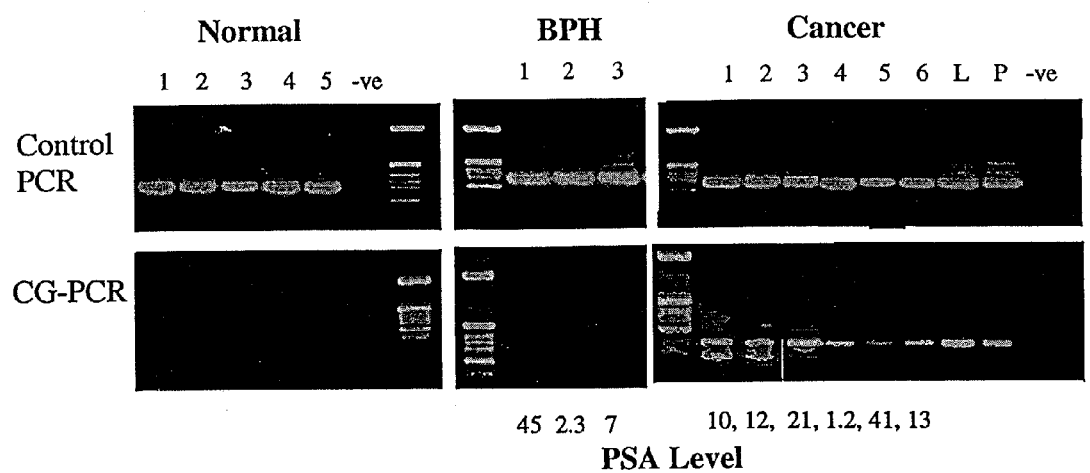

FIG. 8 provides the results of amplification of bisulphite treated DNAs, wherein the DNA has been isolated from blood samples from normal subjects with no known prostate complaint, from patients with benign hyperplasia (BPH) of the prostate and from patients with histologically confirmed prostate cancer.

Figure 9:
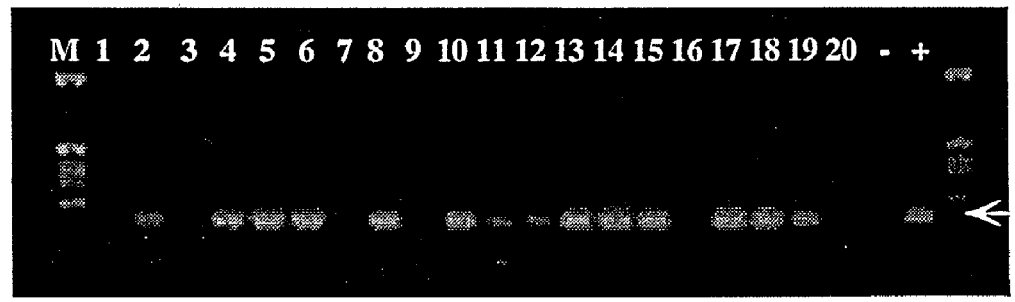

FIG. 9 shows the results of amplification of bisulphite treated DNAs isolated from 20 liver cancer tissue samples. Selective PCR amplification was conducted using the outer primer pair CGPS-5 and 8 and the inner primer pair CGPS-11 and 12.

Figure 10:
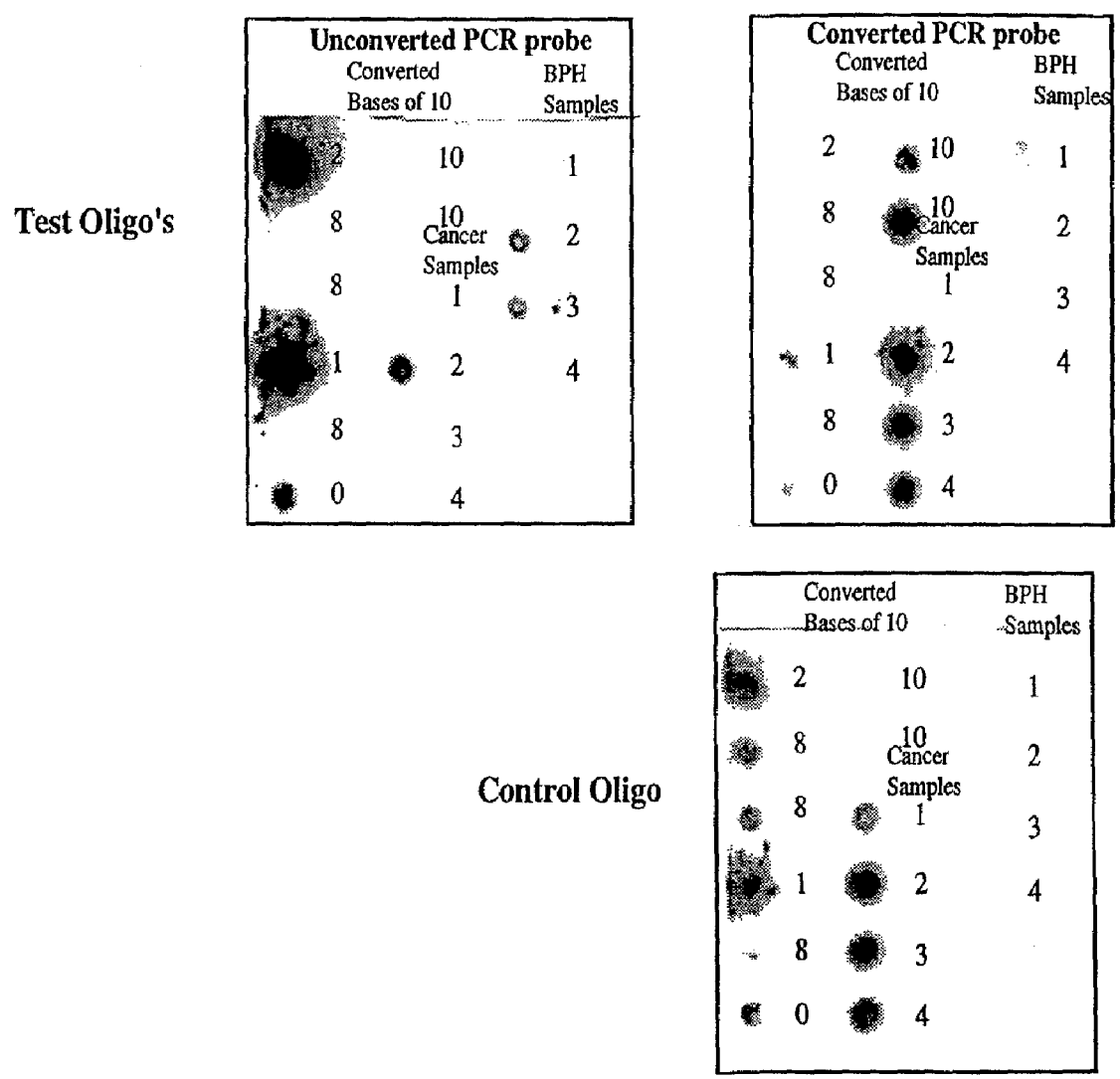

FIG. 10 shows the results of tests conducted to confirm that any amplified DNA products has occurred from amplification of bisulphite treated DNA wherein all unmethylated cytosine has been converted to uracil. The tests are conducted using oligonucleotides probes designed to hybridise to converted or non-converted target regions.

GENERAL METHODS AND STRATEGIES (1) Treatment of DNA with bisulphite

DNA for assaying was isolated from suitable sources by standard protocols and treated with bisulphite by well known methods (12, 13, 16).

(2) Characterisation of Metlhylation of Individual Sites in DNA

In order to determine the methylation status of individual cytosine nucleotides in target and non-target DNAs and to identify differences between them, bisulphite-modified DNA was amplified by PCR using primers designed to minimise the possibility that the methylation status of a particular CpG site will influence primer annealing and subsequent amplification (12, 13, 16).

(3) Design of Selective Primers

Based on the sequencing information, primers for use in the assay were designed to maximise the possibility that the methylation status of a particular CpG site would influence primer annealing and subsequent amplification. Specifically, the design principles followed (described for the "forward" PCR primer where the primer contains the same C to T (or U) conversions as would occur in the bisulphite-treated DNA), are listed below at (a) to (d):

(a) That primers should cover sequence regions which contain a number of C's. Conversion of unmethylated C's to U's provides for discrimination between molecules which have undergone efficient bisulphite conversion and molecules in which C's have not reacted (e.g. because not completely dissolved or containing regions of secondary structure).

(b) That at least one, but preferably at least two to four, of the C's in the regions should be C's (generally at CpG sites) known to be methylated in a high proportion of the DNA to be detected (i.e. target DNA). Thus, these C's will remain C's in the target DNA while being converted to U's in the non-target DNA. A primer which is designed to be the exactly equivalent of the bisulphite-converted methylated DNA will contain a mismatch at each of the positions of an unmethylated C which has been converted to a U in an unmethylated DNA. The more mismatches that are present, the greater the differential hybridisation stability of the primers will be and hence the greater the selective difference in PCR.

(c) That the 3' terminal base of the printer should preferably be a C corresponding to a C known to be methylated in the target DNA (normally part of a CpG dinucleotide). Correct pairing with the terminal base of the primer will provide for highly selective priming of target sequences compared with unmethylated background sequences which will form a C:A mismatch.

(d) That at positions where it is known that methylation occurs in only a fraction of molecules in the methylated target DNA or where it is known to vary between target DNAs (e.g. in different tumour samples), redundancy can be incorporated into the primers to allow for amplification of either C or T from the target DNA. This same approach can be used if polymorphisms are known to exist in the primer region.

For the "reverse" primer, which anneals to the converted strand, A's replace G's at positions opposite converted C's (4) Verification of Selective Target Sequence Amplification The amplified PCR band can be analysed to verify that it has been derived from DNA which has been fully bisulphite-converted (i.e. C's not methylated in the original DNA have been converted to U's and amplified as T's) and to further verify that the amplified DNA has been derived from the specific target DNA sequence and has the expected methylation profile (i.e. 5meC's not converted to T's). Methods for conducting these verifications include:

(a) Using restriction enzyme digestion.

In order to verify complete conversion, particular restriction enzymes can be used to cut the DNA. The sequence recognition sites should have the property that they contain no C's and are present in the sequence of the amplified strand after but not before bisulphite treatment. Thus, the conversion of one or preferably two or more C's to U's and their amplification as T's in the PCR product should produce a new restriction site. Useful enzymes are shown in italics in Table 1 below.

In order to verify that the target DNA sequence amplified was specifically methylated, use can be made of restriction enzyme sites whose only C nucleotides are found as CpG dinucleotides and which, if the sequence was methylated, would remain as CpG's in the PCR products. Examples of such enzymes are shown in bold in Table 1 below. BsmBI, which cuts the non-symmetrical sequence GAGACG can also be used.

In some instances, enzymes which contain a C as an outer base in their recognition sequence can be used for verification of methylation: e.g. EcoRI (GAATTC) for a GAATTCG sequence or Sau3AI (GATC) for a GATCG sequence (bold and underlined in Table 1). If a site such as one of the above is present in the predicted methylated, fully bisulphite-converted DNA then the enzyme will cut the DNA only if the original CpG dinucleotide was methylated, confirming the amplification of a methylated region of DNA. Some of the enzymes (bold and underlined in Table 1) have the potential to be used both for monitoring efficient conversion and CpG methylation.

(b) Differential hybridisation to specific oligonucleotides.

Differential hybridisation to specific oligolnucleotides can be used to discriminate that the amplified DNA is fully reacted with bisulphite and of the expected methylation profile. To demonstrate complete conversion, a pair of oligonucleotides corresponding to the same region within the amplified sequence is prepared. One oligonucleotide contains T's at all C's which should be converted by bisulphite, while the other contains C's in these positions. The oligonucleotides should contain at least two or three of such discriminatory C's and conditions be determined which provide for selective hybridisation of each to its target sequence. Similar oligonucleotides with C or T at CpG sites and T's replacing all non-CpG C's are used to determine whether the specific CpG sites are methylated. Additional control oligonucleotides that contain no discriminatory C's, that is, either no C's or a minimal number where C's are substituted with Y's (mixture of C and T), are used to monitor the amount of PCR product in the sample. The oligonucleotides can be used for direct hybridisation detection of amplified sequences or used to select out target molecules from the PCR-amplified DNA population for other detection methods. An array of such oligonucleotides on a DNA sequencing chip can be used to establish the sequence of the amplified DNA throughout the sequence region.

(c) Single nucleotide primer extension (SNuPE).

The technique of single nucleotide primer extension can be applied to the PCR products to determine whether specific sites within the amplified sequence contain C or T bases. In this method, a primer abutting the position of interest is annealed to the PCR product and primer extension reactions performed using either just dCTP or just dTTP. The products can be separated by gel electrophoresis and quantitated to determine the proportion of each nucleotide in the population at that position. Primers should be designed to quantitate conversion of C's in CpG sites and control C's which should not be methylated. More than one primer can be included in a single reaction and/or run in the same gel track as long as their sizes can be clearly distinguished.

(d) Fluorescent Real-time Monitoring of PCR.

Oligonucleotides internal to the amplified region can be used to monitor and quantify the amplification reaction at the same time as demonstrating amplification of the correct sequence. In the Fluorogenic 5' Nuclease PCR assay (19) the amplification reaction is monitored using a primer which binds internally within the amplified sequence and which contains both a fluorogenic reporter and a quencher. When this probe is bound to its target DNA it can be cleaved by the 5' nuclease activity of the Taq polymerase, separating the reporter and the quencher. By utilising in the assay an oligonucleotide which is selective for the fully bisulphite-converted sequence (and/or its methylation state) both the level of amplification and its specificity can be monitored in a single reaction. Other related systems that similarly detect PCR products by hybridisation can also be used.

EXAMPLE 1

Methylation Sequence Profile of Target and Non-Target GST-PI DNA

Materials and Methods

FIG. 1 shows the organisation of the GST-Pi gene and the regions for which genomic sequencing was used to determine the methylation status of DNA isolated from prostate cancer tissue or cell lines and from normal prostate or other tissues. The nucleotide sequence numbering in FIG. 1 is according to the GST-Pi sequence, Genbank Accession No. M24485. Also shown, within the boxes is the sequence of each amplified region, with all the CpG sites indicated and numbered relative to the position of the transcription start site. Sequence analysis demonstrated that there was an additional CpG dinucleotide (+9) not predicted from the published sequence. Also identified in the regions sequenced was a polymorphism which is present in a significant fraction of the samples studied. The polymorphic allele does not contain CpG site −33. Both the additional CpG dinucleotide and the polymorphism are shown in FIG. 2. The nucleotide coordinates in FIG. 2 are shown relative to the transcription start site; the first base shown, −434, corresponds to base 781 of the Genbank sequence, while the last +90, corresponds to base 1313 of the Genbank sequence.

Table 2 lists the sequences and positions of the non-selective primers used for amplification (Table 2-1) and direct sequencing (Table 2—2) of bisulphite-treated DNA.

DNA isolated from normal prostate tissue, prostate cancer tissue, prostate cancer-derived cell lines and other tissues was bisulphite treated and PCR reactions done by standard procedures (13). PCR products were either digested with informative restriction enzymes, sequenced directly (17), or individual molecules cloned and sequenced by standard procedures.

Results

In FIG. 3A, the methylation status of sites in DNA from prostate cancer cell lines, prostate cancer tissue samples and matched normal prostate tissue are shown for the core promoter regions through to the 3' end of the gene (covering CpG sites −28 to 103). It can be seen that in normal prostate tissue, the core promoter region is unmethylated at all sites and that this lack of methylation extends through the region flanking the promoter to CpG site +33. Results of restriction enzyme digests of bisulphite-treated, PCR-amplified DNA indicate that this lack of methylation includes CpG sites +52 and +53. However, in the regions further downstream which were analysed, CpG sites +668 to +74 and +96 to +103, DNA from normal prostate tissue was heavily methylated. Analysis of the prostate cancer cell line LNCaP and prostate cancer tissue samples demonstrates extensive methylation of the core promoter region; variations in the overall level of methylation probably reflect the presence of different levels of normal cells within the tumour samples. DNA from one cancer sample (2AC) was found to be completely unmethylated and in contrast to the other tumour samples this tumour was found by immunohistochemistry to still be expressing GST-Pi. Sequencing of the region flanking the core promoter in the LNCaP cell line and tumour DNAs, BC and CC, showed that methylation extended through to CpG site +33 and further restriction enzyme analysis showed that methylation included CpG sites +52 and +53. For one tumour sample, DC, methylation did not extend beyond the core promoter region and CpG sites +13 to +33, as well as CpG sites +52 and +53 were found to be unmethylated. It is notable that this tumour was of Gleason Grade 2+2, the lowest grade tumour among those analysed. For all tumour DNA samples, as for the normal DNA, the downstream regions of the gene, sites 68 to 74 and 96 to 103, were heavily methylated. Within the promoter regions which were methylated in the cancer, but not normal, tissue specific individual sites were evident which were either unmethylated or methylated to a much lower degree than surrounding methylated sites. These include sites −22 and −23 (XC), −20 (PC3 lines, XC and WC), −14 (PC3, XC and WC), +24 (PC3-M and MM2, CC), +25 (LNCaP, PC3-MM2, CC).

The results shown in FIG. 3B provides a comparison of the methylation state of the core promoter region and sequences upstream of the core promoter region in DNA isolated from normal prostate tissue and from a number of other normal tissues. Sequences from the PCR fragment upstream of the core promoter were determined by cloning and sequencing as the region is refractory to direct sequencing. For the cancer samples, the level of methylation shown is as a proportion of those clones which were methylated (about 50% of the total clones in both cases). In normal prostate tissue as well as in all other normal tissues there is extensive methylation of CpG sites upstream of the AT-rich repeat. Downstream of the repeat (from CpG site −43) minimal methylation was seen in all normal tissues except normal liver tissue, where there was significant methylation of CpG sites −7 through to +7. Sequences upstream of the core promoter were found to be heavily methylated in the prostate cancer DNAs, though again specific sites were undermethylated; site −32 in cancers B and D and site −36 in cancer B.

The results therefore allow for the identification of a region of the GST-Pi gene and its regulatory flanking sequences, stretching from 3' of the polymorphic repeat region, (CpG site −43) to sites +52 and +53, which is not methylated in normal prostate tissue but is normally highly methylated in prostate cancer. In one cancer sample (D, the cancer of lowest Gleason Grade) the region from CpG sites +13 to +53 was not methylated. The more restricted region extending from CpG site −43 to +10 was methylated in all of the prostate cancer DNAs which showed promoter methylation. Methylation of part of the promoter region (CpG sites −7 to +7) was also seen in one normal tissue (liver) examined. Analysis of further samples of normal liver DNA has shown that the level of methylation is variable and can include CpG sites from −13 to +8.

Discussion

The above results are critical in identifying regions within the GST-Pi gene and/or its regulatory flanking sequences which can be used for the development of assays for the selective detection of prostate cancer cells. Thus, the region from CpG sites −43 to +53 lying within the boundary of regions methylated in normal prostate tissue can be used for the design of primers to detect cancer-specific methylation in prostate tissue samples. The region from CpG site −43 to +10 is preferred for the detection of a higher proportion of cancers. The region from CpG sites +13 to +53 may be used to detect cancer but also may be used to distinguish early (unmethylated) cancer from later (methylated cancer). For assays using other samples, such as blood, it is preferred to restrict the region chosen to exclude CpG sites −7 to +7 or, more preferably sites −13 to +8. For example, liver cells may be present in the blood taken from a subject suffering liver disease, in which case, a false positive result could be obtained if the region chosen for detection of cancer-specific methylation includes CpG sites −13 to +8.

EXAMPLE 2

Design and Use of Selective Primers for Detection of Methylated GST-Pi DNA

Materials and Methods

Sequence primers for the detection of methylated GST-Pi sequences from three regions, namely a region upstream of the core promoter (primers CGPS-5 to 9 and CGPS-11 to 13), a region partially encompassing the core promoter (primers CGPS-1 to 4), and a region further downstream from the core promoter (primers CGPS-21 to 24) are shown in Table 3 below.

The sequence and derivation of primers for the upstream region are shown in FIG. 2 (from CpG site −43 to CpG site +10), which also shows the common polymorphism encompassing CpG site −33 (see above the sequence (p)). Underneath is shown the sequence of the derived strand after conversion of cytosines to uracil. The derived strand is shown either assuming all CpGs are methylated (B-M) or that none are (B-U). Below this is shown specific primers designed to selectively amplify the methylated sequence. It can be seen that all primers are designed to match perfectly to the treated, methylated template, but contain mismatches to the template derived from unmethylated DNA or the original untreated DNA. Primers CGPS-5, 8, 11, 12 and 13 are designed to avoid the polymorphic region and CpG sites which show a lower frequency of methylation in prostate cancer DNAs. The underlined T's in the forward primers (and A's in the reverse primers) derive from bisulphite conversion of C's and provide discrimination against amplification of DNA which has not been efficiently converted by the bisulphite treatment. The bold C's in the forward primers (and G's in the reverse primers) are parts of CpG sites and will form base pairs with DNA derived from methylated sequences but form mismatches to DNA derived from unmethylated sequences. Redundancy is included in some positions, Y (mix of C and T) in forward primers and R (=mix of A and G) in reverse primers to allow pairing independent of methylation status. This can allow for certain sites where the frequency of methylation within or between tumour samples is variable (eg. site −14). Forward and reverse primers for specific selective amplification of methylated GST-Pi sequences are shown in Table 3 below.

Amplifications conducted for this example, utilised bisulphite treated DNAs from a variety of tissues and used two sets of PCR primers. Specifically, for the amplification reactions shown in FIG. 4A Panel A (region covering the transcription start site), CGPS-1 and 3 were used as outer primers and CGPS-2 and 4 as inner primers. For the amplification reactions shown in FIG. 4A Panel B and FIGS. 4B and 4C, the outer primer pair, CGPS-5 and CGPS-8 which encompass the region from CpG site −39 to −16, were used for first round amplification, followed by second round amplification with the CGPS-6 and CGPS-7 primers, resulting in the amplification of a 140 bp fragment covering CpG sites −36 to −23. For the amplification reactions shown in FIGS. 5 to 8, the primer set used for the upstream region was the outer primer pair, CGPS-5 and CGPS-8, for first round amplification and the inner primer pair, CGPS-11 and CGPS-12, for second round amplification, resulting in the amplification of a 167 bp fragment covering CpG sites −38 to −23.

For all sets of primers, PCR amplifications were performed in a buffer consisting of 67 mM Tris/HCl, 16.6 mM ammonium sulphate, 1.7 mg/ml BSA and 1.5 mM MgCl$_2$, prepared in TE buffer (10 mM Tris/HCl pH 8.8, 0.1 mM EDTA). Reaction mixes (50 µl) contained 200 µM of each of the four dNTPs, 6 ng/ml of each primer and 2 units of AmpliTaq DNA polymerase (Perkin Elmer). For the primers CGPS-5 and 8 (first round amplification), PCR cycle conditions were 5 cycles of 60° C. 1 min., 72° C. 2 min. and 95° C. 1 min., followed by 30 cycles of 65° C. 1 min., 72° C. 1.5 min. and 95° C. 1 min. Amplification conditions for the primers CGPS-6 and 7 (second round amplification) were 5 cycles of 65° C. 1 min., 72° C. 2 min. and 95° C. 1 min., followed by 30 cycles of 65° C. 1 min., 72° C. 1.5 min. and 95° C. 1 min. For the primers CGPS-11 and 12, the amplification conditions were the same as for the CGPS-6 and 7 primers except that the annealing temperature was raised from 65° C. to 70° C. 2 µl of the first round amplification reactions were used in 50 µl of second round amplification reactions. Other buffers or PCR amplification conditions may also be used to achieve similar efficiency and specificity.

Results and Discussion

For the primers covering the core promoter region (see FIG. 4A Panel A), amplified DNA (see arrowed band) was obtained from the positive control DNA (cancer B) but also from DNA from prostate tissue samples from two subjects who had not been diagnosed with prostate cancer. Bands of amplified DNA were also seen from DNA isolated from a bone marrow and blood sample as well as from DNA isolated from liver tissue samples from subjects with no known prostate cancer.

For the upstream amplification (see FIG. 4A Panel B), no amplified DNA was obtained from amplification reactions conducted on DNA isolated from a range of healthy tissue samples nor from DNA isolated from blood samples of subjects with no known prostate cancer; a band of amplified DNA was produced from the positive control DNA (cancer B). However, while amplification reactions conducted on DNA isolated from one normal prostate tissue sample did not result in amplified DNA, amplified DNA did result from the same amplification reactions conducted on DNA isolated from a prostate tissue sample of an 82 year old subject with no known prostate cancer. It is possible that this subject had undiagnosed prostate cancer. DNA isolated from five other samples of normal prostate tissue from subjects with no known prostate cancer did not give rise to an amplified DNA product (see FIG. 4C Panel B).

Figure 4B:
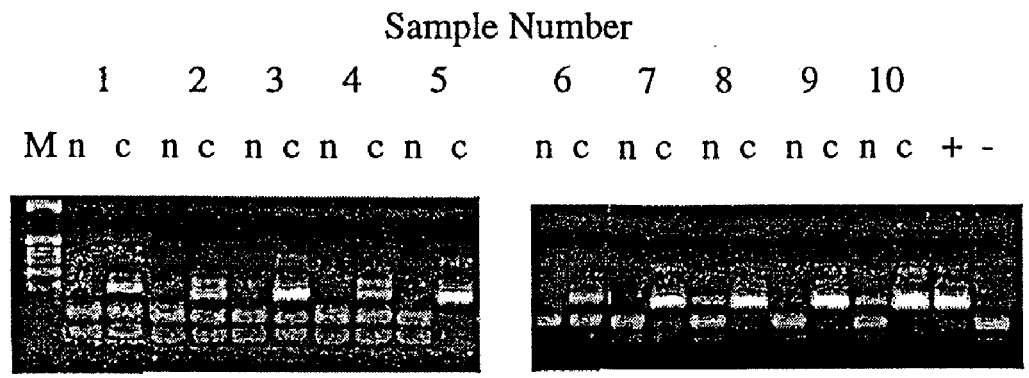

In FIG. 4B, the results of PCR amplification reactions are shown for tissue samples from patients with prostate cancer: for each sample, DNA was isolated from a region identified as containing cancer and from another region identified as grossly normal. In all cases, a clear band of amplified DNA was produced from amplification reactions conducted on prostate cancer DNA. Two of these, were cases where the proportion of methylated DNA was insufficient to be detected using primers designed to prime equivalently on methylated and unmethylated DNA. For DNA isolated from grossly normal tissue, the band of amplified DNA was either absent or present in a substantially lower amount. The presence of a band in some "normal" samples could derive from a low level of cancer cells in the sample.

Amplification of DNA from samples of blood obtained from the abdominal cavity during surgery showed that it was possible to detect methylated GST-Pi sequences in a number of them. Samples of peripheral blood isolated from three patients with known metastatic disease (see FIG. 4C Panel B) demonstrated the presence of amplifiable, methylated GST-Pi sequences.

Amplified DNA products were also produced from amplification of DNA isolated from the LNCaP and DU145 prostate cancer cell lines, but not from the PC-3 series of cell lines. This latter result could be due to a low level of methylation in the upstream promoter region in PC-3 cells, but a major contributing factor is likely to be a lack of priming by the CGPS-6 primer as PC-3 only contains the variant allele of the GST-Pi gene. Methylated GST-Pi sequences were also detected in DNA isolated from some tumour-derived cell lines of non-prostatic origin: HeLa, a cervical carcinoma, and HepG2, a liver carcinoma (see FIG. 4C Panel B).

DNA was isolated from the seminal fluid (see FIG. 5) of 3 prostate cancer patients (C) and from 5 subjects with no known prostate cancer (N), treated with bisulphite and amplified using primers CGPS-5 and 8 followed by CGPS-6 and 7. Amplified DNA products were obtained from all three cancer DNAs. One of the five samples from subjects without diagnosed prostate cancer also resulted in an amplified DNA product, but it is not clear if this represents a false positive or a case of undiagnosed prostate cancer in the particular subject.

The use of the primer CGPS-11 avoids annealing across the polymorphic sequence at CpG site −33, and the combination of CGPS-5 and 8 as outer primers followed by CGPS-11 and 12 as inner primers was found to give efficient amplification of prostate cancer DNA. In a first experiment (see FIG. 6), DNA was extracted from regions of fixed tissue slides that had been identified as either being cancerous or being diseased with benign hyperplasia (BPH). DNA was isolated by incubating scraped material in 400 µl of 7M guanidinium hydrochloride, 5 mM EDTA, 100 mM Tris/HCl pH 6.4, 1% Triton-X100, 50 mg/ml proteinase K and 100 mg/ml yeast tRNA. After homogenisation, samples were incubated for 48 hours at 55° C. then subjected to five freeze/thaw cycles of dry ice for 5 min./95° C. for 5 min. After vortexing and centrifugation for 2 min. in a microfuge, the supernatants were then diluted three fold, extracted with phenol/chloroform and ethanol precipitated. DNA isolated from samples from 6 cancer patients and 4 with BPH were amplified with either non-selective primers for the core promoter region (i.e. control PCR amplification with GST-9 and 10 followed by GST-11 and 12) or CG selective primers (i.e. selective PCR amplification with CGPS-5 and 8 followed by CGPS-11 and 12). Control PCR amplifications demonstrated the presence of amplifiable DNA in all samples. Using the CG selective primers, amplified DNA products were only obtained from the cancer DNAs. The PSA (prostate specific antigen) levels of these patients ranged from 4 to 145 ng/ml. For the BPH patients, the PSA levels ranged from 2.3 to 25 ng/ml.

In further experiments, prostate cancer cells were first enriched from blood samples using antibodies coupled to magnetic beads followed by DNA isolation, bisulphite modification and PCR amplification. Cell isolation was achieved using Dynabeads anti-Epithelial Cell (Dynal Prod. No. 112.07) essentially as described by the manufacturer. The magnetic beads were coated with the anti-epithelial antibody in Ab Ber-EP4 (22). Alternatively, magnetic beads coupled to antibodies specific for the extracellular domain of the prostate specific membrane antigen (23) could have been used. Whole blood was diluted 1:1 with Dulbecco's phosphate buffered saline (PBS) containing 10 mM EDTA and 40 μl of pre-washed magnetic beads added. Cells were incubated at 4° C. on a rotating platform for 30 min and then the beads were collected to the side of the tube using a magnetic cell separation device for 4 min. The supernatant was then carefully aspirated and the beads resuspended in the washing solution (PBS containing 0.5% bovine serum albumin). Beads were then again collected to the side of the tube using a magnet and the supernatant carefully aspirated before conducting a further wash was done with the tube remaining in place in the magnetic separation device and the supernatant aspirated. The beads were then resuspended in DNA isolation buffer (100 mM Tris/HCl pH 8, 25 mM EDTA, 1% Sarkosyl, 200 mg/ml proteinase K), incubated for at least 2 h at 370 and DNA recovered by phenol/chloroform extraction and ethanol precipitation. The DNA was then finally subjected to bisulphite treatment and PCR amplification.

Figure 7A:
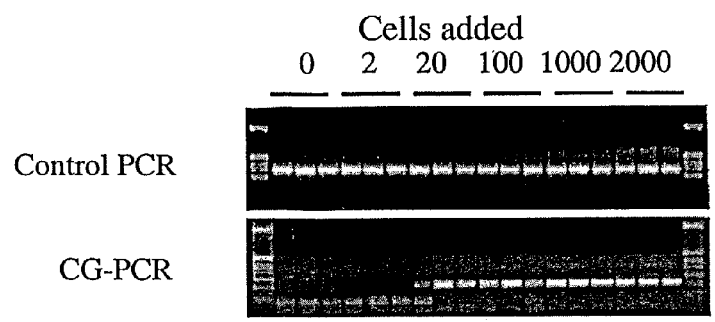
Figure 7B:
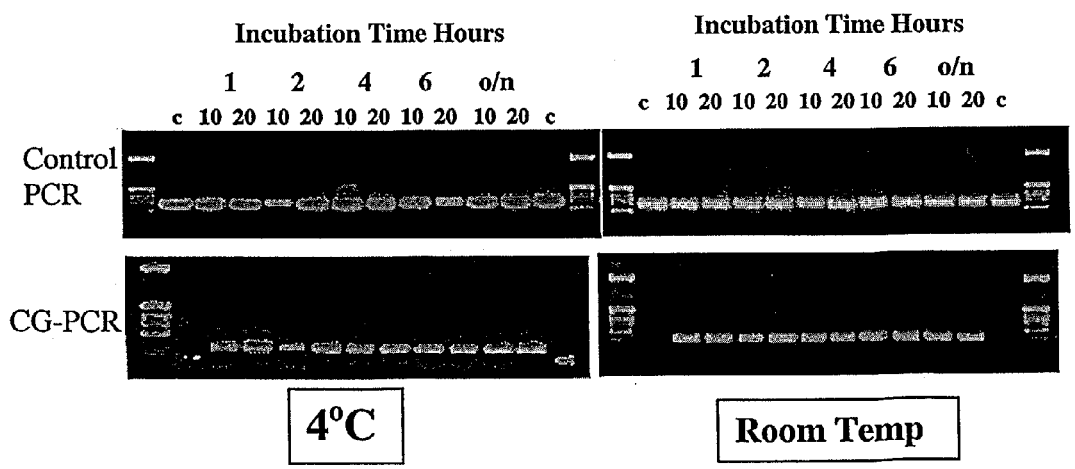

The sensitivity of this method was tested by seeding varying numbers of cells of a prostate cancer cell line, LNCaP, into normal blood. As shown in FIG. 7A, the presence of 20 cells or more in 0.5 ml of blood could be reliably detected. The experiment shown in FIG. 7B showed that blood samples containing LNCaP cells could be stored at room temperature or at 4° C. for up to 24 hours without loss of sensitivity.

Using magnetic bead capture followed by bisuliphite treatment and selective PCR amplification, patient blood samples were also analysed and the results from a set of these are shown in FIG. 8. These include blood samples from normal subjects with no known prostate complaint, from patients with benign hyperplasia (BPH) of the prostate and from patients with histologically confirmed prostate cancer. The control PCR amplifications (upper panel) used primers which amplify both methylated and unmethylated GST-Pi sequences. The amplifications using CG-selective primers are shown in the lower panel. Positive control amplifications (LNCaP (L) and PC3 (P)) are shown in the cancer panels and negative control amplifications are shown in the normal and cancer panels.

Table 4 below summarises the results of testing of DNA from patient blood samples using the magnetic bead/CG selective PCR amplification protocol. No amplified DNA products were obtained from DNA isolated from normal control subjects, and only DNA isolated from one of 18 patients diagnosed histologically to have BPH produced amplified DNA products (this patient had a blood PSA level of 17 ng/ml). Of patients with confirmed prostate cancer, isolated DNA from 17 of 24 (70%) were PCR-positive (i.e. resulted in the production of amplified DNA), indicating the presence of prostate cancer cells in the blood. For patients clinically staged as A and B, (i.e. disease confined to the prostate), cancer cells were detected in the blood in 6 of of the 10 cases. For 9 patients with locally invasive (Stage C) or metastatic (Stage D) disease, cancer cells were detected in the blood in every case.

Since it was found that the HepG2 liver cancer cell line contained methylated GST-Pi sequences, samples of DNA isolated from liver cancer tissue was also examined. DNA isolated from 20 liver cancer samples were bisulphite treated and amplified using the CGPS-5 and 8 and CGPS-11 and 12 primer pairs (see FIG. 9). 14 of the 20 samples were PCR-positive. On the other hand, no amplified DNA products were produced from DNA isolated from 2 patients with no liver cancer (see FIG. 4 and data not shown). DNA isolated from normal liver tissue was shown to be partially methylated in the region of the transcription start site (CpG sites −7 to +7, see FIG. 3B). Analysis of further samples of normal liver DNA has shown that the level of methylation is variable and can include CpG sites from −13 to +8. The primer pairs used here encompass CpG sites −39 to −16, upstream of the region of methylation seen in normal liver DNA.

The above results show that different sets of primers designed to hybridise the core promoter of the GST-Pi gene or the region upstream of the core promoter, call reliably amplify bisulphite-treated DNA that has been isolated from prostate cancer cells. However, primers designed to hybridise to the core promoter are less selective in that DNAs isolated from a number of normal tissue samples result in amplified DNA products. Thus, primers designed to hybridise to regions found to be unmethylated in DNA from normal tissues, that is, the upstream region encompassing CpG sites −45 to −8 and the region downstream of the promoter encompassing CpG sites +8 to +53, are preferred for the prognostic or diagnostic assaying of prostate cancer. Additionally, primers designed to hybridise to this latter region may also be useful for discriminating between early and late prostate cancer.

EXAMPLE 3

Confirmation of Correct Amplification

The specific oligonucleotides probes described below can be used to confirm that any amplified DNA products resulting from the amplification step of the assay is due to DNA in which all unmethylated cytosines had been converted to uracils. Those for the upstream PCR region can be used with amplified DNA products from all combinations of the CGPS-5, 6, 11, 7 to 9, 12 and 13 forward and reverse primers. Those for the downstream PCR region can be used with amplified DNA products of the CGPS-21 to 24 primers. A biotinylated version of the conversion-specific olignucleotide can also be used for the selective and specific capture from solution of the amplified DNA products generated using these primer pairs, or the appropriately labelled oligonucleotide can be use for real-time monitoring of specific PCR fragment amplification. Amplified DNA products from PCR amplification of bisulphite-treated DNA routinely have one strand containing a very high proportion of thymine nucleotides and the other strand containing a very high proportion of adenine nucleotides. Because of this, it is possible to use oligo dT (or oligo dA) as a generic conversion specific oligonucleotide, the annealing conditions being varied to optimise discrimination of converted and non-converted DNA for each PCR fragment.

Upstream PCR Region:

Conversion Oligonucleotide:
    HybC5 5'-AAACCTAAAAAATAAACAAACAA (SEQ ID NO: 17)

Non-Conversion Oligonucleotide:
    HybU5 5'-GGGCCTAGGGAGTAAACAGACAG (SEQ ID NO: 18)

Conversion Neutral Oligonucleotide:
    HybN5:    5'-CCTTTCCCTCTTTCCCARRTCCCCA (SEQ ID NO: 19)

Downstream PCR Region:

Conversion Oligonucleotide:
    HyBC3 5'-TTTGGTATTTTTTTTCGGGTTTTAG (SEQ ID NO: 20)

Non-Conversion Oligonucleotide:
    HybU3    5'-CTTGGCATCCTCCCCCGGGCTCCAG (SEQ ID NO: 21)

Conversion Neutral Oligonucleotide:
    HybN3 5'-GGYAGGGAAGGGAGGYAGGGGYTGGG (SEQ ID NO: 22)

To demonstrate the selectivity of such hybridisations, a series of DNAs were spotted onto nylon membranes and hybridised with conversion and non-conversion specific oligonucleotide probes for the upstream PCR region as well as a control oligonucleotide. The DNAs included:
(i) individual cloned PCR products from amplification of the upstream region that contained differing numbers of converted cytosines in the region complementary to the probe (see FIG. 10, where the number of converted cytosines, out of 10, is shown (Column 1 and top 2 spots of Column 2). n.b. the two clones containing 10/10 converted bases end adjacent to and do not contain the sequences complementary to the control oligonucleotide); and
(ii) PCR products from cancer patients and patients with benign hyperplasia that had been amplified from bisulphite-treated DNA using CG-selective primers (CGPS-5 and 8, followed by CGPS 11 and 12) (see FIG. 10, where these are labelled as Cancer Samples 1 to 4 (lower part of column 2) and BPH samples 1 to 4 (Column 3)).

Hybridisations with kinased oligonucleotide probes were performed in Express-Hyb buffer (Clon tech) at 45° C. for two hours followed by four 20 min. washes in 2×SSC, 0.1% SDS at 45° C. before phosphorimage analysis.

Hybridisations with the control oligonucleotide probes provides an estimate of the amount of DNA in the sample. As expected, none of the PCR amplifications of BPH samples produced significantly detectable product, while 3 of 4 cancer samples gave a strong signal and one a very weak one.

Hybridisations with the conversion-specific probe showed a clear signal for the plasmid DNAs that matched the probe perfectly and for the 3 cancer samples for which there was stronger hybridisation with the control oligonucleotide probe. The fourth cancer sample that gave a very weak signal with the control oligonucleotide was barely detectable with the conversion-specific probe. This could have been due to the low level of DNA or, possibly, the presence of partially-converted DNA molecules. None of the plasmid clones that had mismatches to the conversion-specific probe gave a significant signal. The probe for unconverted DNA hybridised clearly with plasmid DNAs that had 0, 1 or 2 bases converted, but not with samples that had 8 or 10 converted bases. The hybridisations also indicated that there was a low level amplification of unconverted DNA in two BPH and one cancer sample (in this latter case there was a strong signal from probe for fully converted DNA, indicating that the PCR product was predominantly derived from properly converted DNA).

The results show that oligonucleotides of the type used here can discriminate between molecules that have been efficiently converted by bisulphite and those that have not. They can be used in a number of formats for detection of PCR products or prior to PCR or other detection methods to select out efficiently converted molecules of the target region from the total DNA population. The same approach can be used with primers that distinguish CpG methylated DNAs (or their derivatives containing C's) from unmethylated DNAs (containing U's or their derivatives containing T's).

REFERENCES

1. H. S. Shapiro, *Content of 6-methylaminopurine and 5-methylcytosine in DNA*. G. D. Fasman, Ed., Handbook of Biochemistry, Selected Data for Molecular Biology: Nucleic Acids. (CRC Press, Boca Raton Fla., 1975).
2. R. L. Adams, Burdon, R. H., Molecular Biology of DNA methylation (Springer Verlag, New York, 1985).
3. Y. Gruenbaum, T. Naveh-Many, H. Cedar, A. Razin, *Nature* 292, 860–862 (1981).
4. S. J. Clark, J. Harrison, M. Frommer, *Nat Genet* 10, 20–27 (1995).
5. R. Holliday, J. E. Pugh, *Science* 187, 226–232 (1975).
6. A. D. Riggs, *Cytogenet. Cell Genet.* 14, 9–25 (1975).
7. M. Graessmann, A. Graessmann, in *DNA Methylation: Molecular Biology and Biological Significance* J. P. J. H. P. Saluz, Ed. (Birkhauser Verlag, Basel, Switzerland, 1993) pp. 404–424.
8. C. Stirzaker, et al., *Cancer Res* 57, 2229–2237 (1997).
9. K. D. Tremblay, K. L. Duran, M. S. Bartolomei, *Mol Cell Biol Molecular and Cellular Biology* 17, 4322–4329 (1997).
10. R. Y.-H. Wang, Gehrke, C. W. and Ehrlich, M., *Nucl. Acids Res.* 8, 4777–4790 (1980).
11. R. Shapiro, B. Braverman, J. B. Louis & R. E. Servis, *J. Biol. Chem.* 248, 4060–4064 (1973).
12. M. Frommer, McDonald, L. E., Millar, D. S., Collis, C. M., Watt, F., Grigg, G. W., Molloy, P. L. & Paul, C. L., *Proc. Natl. Acad. Sci. USA.* 89, 1827–1831 (1992).
13. S. J. Clark, Harrison, J., Paul, C. L., & Frommer, M., *Nucl. Acids Res.* 22, 2990–2997 (1994).
14. J. G. Herman, J. R. Graff, S. Myohanen, B. D. Nelkin &S. B. Baylin, *Proc Nat Acad Sci USA* 93, 9821–9826 (1996).
15. W. H. Lee, et al., Proc Natl Acad Sci USA 91, 11733–11737 (1994).
16. S. J. Clark, M. Frommer, in *Laboratory Methods for the detection of mutations and polymorphisms in DNA*. G. Taylor, Ed. (CRC press, NewYork, 1997) pp. 151–162.
17. C. L. Paul, S. J. Clark, *BioTechniques* 21, 126–133 (1996).
18. W. H. Lee, W. B. Isaacs, G. S. Bova & W. G. Nelson, *Cancer Epidemiol Biomarkers Prev.* 6, 443–450 (1997).
19. P. M. Holland, R. D. Abramson, R. Watson & D. H. Gelfland, *Proc. Natl. Acad. Sci. USA* 88, 7276–7280 (1991).
20. F. Barany, *Proc. Natl. Acad. Sci. USA* 88, 189–193 (1991).
21. R. D. Abramson and T. W. Myers, *Curr. Opinion Biotechnol.* 4, 41–47 (1993).
22. U. Latza, G. Niedobitek, R. Schwarting, H. Nekarda and H. J. Stein, *Clinical Pathology* 43, 213–219 (1990).

23. H. Liu, P. Moy, S. Kim, Y. Xia, A. Rajasekaran, V. Navarro, B. Knudsen and N. H. Bander, *Cancer Res.* 57, 3629–3634 (1997).

TABLE 1

|   |   |   |   |   |   |   | AATT | TTAA | ATAT | ACGT | CGCG | GATC | TCGA | AGAG |
|---|---|---|---|---|---|---|------|------|------|------|------|------|------|------|
| ↓ |   |   |   |   |   |   | Tsp509I |   |   | Mae II |   | Sau3A |   |   |
|   | o | o | o | o |   |   |   |   |   |   |   |   |   |   |
|   | ↓ |   |   |   |   |   |   | Mse I |   |   |   |   | Taq I |   |
|   | o | o | o | o |   |   |   |   |   |   |   |   |   |   |
|   |   | ↓ |   |   |   |   |   |   |   |   | BstUI |   |   |   |
|   | o | o | o | o |   |   |   |   |   |   |   |   |   |   |
|   |   |   | ↓ |   |   |   |   |   |   | Tai I |   |   |   |   |
|   | o | o | o | o |   |   |   |   |   |   |   |   |   |   |
| ↓ |   |   |   |   |   |   | Apo I |   |   |   |   |   |   |   |
| A | o | o | o | o | T |   |   |   |   |   |   |   |   |   |
|   | ↓ |   |   |   |   |   |   | Ase I |   |   |   |   |   |   |
| A | o | o | o | o | T |   |   |   |   |   |   |   |   |   |
|   |   | ↓ |   |   |   |   |   |   | Ssp I |   |   |   |   |   |
| A | o | o | o | o | T |   |   |   |   |   |   |   |   |   |
|   |   |   | ↓ |   |   |   |   |   |   |   |   |   | BstBI |   |
| T | o | o | o | o | A |   |   |   |   |   |   |   |   |   |
|   | ↓ |   |   |   |   |   |   |   |   | Sna BI | Nru I |   |   |   |
| T | o | o | o | o | A |   |   |   |   |   |   |   |   |   |
|   |   | ↓ |   |   |   |   |   |   |   |   |   | Pvu I |   |   |
| C | o | o | o | o | G |   |   |   |   |   |   |   |   |   |
| ↓ |   |   |   |   |   |   | EcoRI |   |   |   |   |   |   |   |
| G | o | o | o | o | C |   | Apo I |   |   |   |   |   |   |   |

TABLE 2.1

Primers for PCR Amplification of the Bisulphite-Modified GST-Pi Gene

| PCR # | Target | Primer Name | Primer Type | Primer 5'          3' | Target size (bp) | Anneal ° C. | Genomic Position |
|---|---|---|---|---|---|---|---|
| −1 | Upstream Top Strand DNA | GST-1 | Outer | TTATGTAATAAATTTGTATATTTTGTATATG (SEQ ID NO: 23) | 646 | 50/50 | 381–411 |
| | | GST-25 | Inner | TGTAGATTATTTAAGGTTAGGAGTT (SEQ ID NO: 24) | 499 | 50/50 | 495–519 |
| | | GST-3 | Inner | AAACCTAAAAAATAAACAAACAACAAA (SEQ ID NO: 25) | 499 | 50/50 | 967–993 |
| | | GST-4 | Outer | AAAAAACCTTTCCCTCTTTCCCAAATCCC (SEQ ID NO: 26) | 646 | 50/50 | 999–1027 |
| 1 | Exon 1 Top Strand DNA | GST-9 | Outer | TTTGTTGTTTGTTTATTTTTTAGGTTT (SEQ ID NO: 27) | 346 | 45/50 | 967–993 |
| | | GST-11 | Inner | GGGATTTGGGAAAGAGGGAAAGGTTT (SEQ ID NO: 28) | 307 | 45/50 | 999–1025 |
| | | GST-12 | Inner | ACTAAAAACTCTAAACCCCATCCC (SEQ ID NO: 29) | 307 | 45/50 | 1280–1303 |
| | | GST-10 | Outer | AACCTAATACTACC TTAACCCCAT (SEQ ID NO: 30) | 346 | 45/50 | 1304–1329 |
| 2 | Exon 1 Bottom Strand DNA | GST-B1 | Outer | AATCCTCTTCCTACTATCTATTTACTCCCTAAA (SEQ ID NO: 31) | 387 | 50/55 | 958–990 |
| | | GST-B2 | Inner | AAAACCTAAAAAAAAAAAAAAAAACTTCCC (SEQ ID NO: 32) | 314 | 50/55 | 999–1027 |
| | | GST-B3 | Inner | TTGGTTTTATGTTGGGAGTTTTGAGTTTT (SEQ ID NO: 33) | 314 | 50/55 | 1285–1313 |
| | | GST-B4 | Outer | TTTTGTGGGGAGTTGGGGTTTGATGTTGT (SEQ ID NO: 34) | 387 | 50/55 | 1317–1345 |
| 3 | Exon 2/Exon 3 Top Strand DNA | GST-13 | Outer | GGTTTAGAGTTTTTAGTATGGGGTTAATT (SEQ ID NO: 35) | 691 | 45/50 | 1287–1315 |
| | | GST-14 | Inner | TAGTATTAGGTTAGGGTTTT (SEQ ID NO: 36) | 603 | 45/50 | 1318–1337 |
| | | GST-15 | Inner | AACTCTAACCCTAATCTACCAACAACATA (SEQ ID NO: 37) | 603 | 45/50 | 1920–1892 |
| | | GST-16 | Outer | CA AAAAACTTTAAATAAACCCTCCTACCA (SEQ ID NO: 38) | 691 | 45/50 | 1978–1950 |
| 4 | Exon 5 Top Strand DNA | GST-30 | Outer | GTTTTGTGGTTAGGTTGTTTTTTAGGTGTTAG (SEQ ID NO: 39) | 340 | 55/60 | 2346–2376 |
| | | GST-31 | Inner | GTTTTGAGTATTTGTTGTGTGGTAGTTTTT (SEQ ID NO: 40) | 265 | 40/45 | 2381–2416 |
| | | GST-32 | Inner | TTAATATAAATAAAAAAAAATATATTTACAA (SEQ ID NO: 41) | 265 | 40/45 | 2617–2646 |
| | | GST-33 | Outer | CAACCCCCAATACCCAACCCTAATACAAATACTC (SEQ ID NO: 42) | 340 | 55/60 | 2653–2686 |
| 5 | Exon 7 Top Strand DNA | GST-26 | Outer | GGTTTTAGTTTTTGGTTGTTTGGATG (SEQ ID NO: 43) | 347 | 50/55 | 3845–3869 |
| | | GST-27 | Inner | TTTTTTTGTTTTTAGTATATGTGGGG (SEQ ID NO: 44) | 287 | 50/55 | 3874–3899 |
| | | GST-28 | Inner | ATACTAAAAAAAACTATTTTCTAATCCTCTA (SEQ ID NO: 45) | 287 | 50/55 | 4161–4132 |
| | | GST-29 | Outer | CCAAACTAAAAACTCCAAAAAACCACTAA (SEQ ID NO: 46) | 347 | 50/55 | 4192–4164 |

Bases arising due to C to U conversion by bisulphite treatment are shown in bold

TABLE 2.2

Primers for Direct Sequencing of Amplified GST-Pi Gene PCR Fragments

| PCR # | Target | Primer Name | Primer Type | Primer 5'          3' | Target size (bp) | Anneal ° C. | Genomic Position |
|---|---|---|---|---|---|---|---|
| 1 | Exon 1 Top Strand DNA | GST-11 | M13 | TGTAAAACGACGGCCAGTGGGATTTGGGAAAGAGGGAA (SEQ ID NO: 47) | 307 | 45/50 | 1003–1026 |
| | | GST-12 | Biotin | BioACTAAAAACTCTAAACCCCATCCC | 307 | 45/50 | 1288–1313 |
| 2 | Exon 1 Bottom Strand DNA | GST-B2 | M13 | TGTAAAACGACGGCCAGTTGTTGGGAGTTTTGAGTTTT (SEQ ID NO: 48) | 314 | 50/55 | 999–1027 |
| | | GST-B2 | Biotin | BioAAAACCTAAAAAAAAAAAAAAAAACTTCCC | 314 | 50/55 | 1285–1313 |
| 3 | Exon 2/3 Top Strand DNA | GST-14 | M13 | TGTAAAACGACGGCCAGTTAGTATTAGGTTA (SEQ ID NO: 49) | 603 | 45/50 | 1317–1337 |
| | | GST-15 | Biotin | BioAACTCTAACCCTAATCTACCAACAACATA | 603 | 45/50 | 1920–1892 |
| 4 | Exon 4/5 Top Strand DNA | GST-31 | M13 | TGTAAAACGACGGCCAGTGTTTTGAGTATTTGTTGTG (SEQ ID NO: 50) | 265 | 55/60 | 2381–2410 |
| | | GST-32 | Biotin | BioTTAATATAAATAAAAAAAATATATTTACAA | 265 | 55/60 | 2617–2646 |

TABLE 4

|  | Assay negative | Assay positive |
|---|---|---|
| Normal subjects | 10 | 0 |
| Benign hyperplasia | 17 | 1 |
| Cancer (total) | 7 | 17 |
| Stage A | 1 | 3 |
| Stage B | 3 | 3 |
| Stage C | 0 | 2 |
| Stage D | 0 | 7 |
| Stage not defined | 3 | 2 |

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

---

The invention claimed is:

1. A method for diagnosing prostate cancer in a subject suspected of having prostate cancer, comprising:
   detecting, in a tissue or body fluid sample from said subject, the presence of an abnormally methylated cytosine in the glutathione S-transferase (GST) Pi gene, wherein the presence of said abnormally methylated cytosine is indicative of prostate cancer; and
   wherein said abnormally methylated cytosine is within a CpG site located within a region defined by and including nucleotides 1232 to 1942 (CpG sites +1 to +55) of SEQ ID NO: 60.

2. The method of claim 1, wherein said abnormally methylated cytosine is within a CpG site located within a region defined by and including nucleotides 1273 to 1942 (CpG sites +9 to +55) of SEQ ID NO: 60.

3. The method of claim 1, wherein the presence of at least two abnormally methylated cytosines are detected, the presence of which are indicative of prostate cancer.

4. The method of claim 1, wherein said detecting comprises the steps of:
   (i) treating DNA, obtained from a tissue or body fluid sample of said subject, so that unmethylated cytosines in the DNA are converted to uracil or another nucleotide capable of forming a base pair with adenine, while methylated cytosines in the DNA are left unchanged or are converted to a nucleotide capable of forming a base pair with guanine, wherein said DNA comprises said glutathione S-transferase (GST) Pi gene;
   (ii) carrying out an amplification reaction of a target region within said GST-Pi gene using the resulting treated DNA of step (i) as a template, wherein said target region is amplified only when said abnormally methylated cytosine is left unchanged or is converted to a nucleotide capable of forming a base pair with guanine as a result of said treating in step (i), and
   (iii) determining if said target region is amplified in step (ii), wherein amplification of the target region is indicative of the presence of said abnormally methylated cytosine in said sample, thereby diagnosing said prostate cancer.

5. The method of claim 4, wherein the amplifying step involves polymerase chain reaction (PCR) amplification.

6. The method of claim 5, wherein said PCR amplification reaction uses a reverse primer having guanine at at least one site whereby, upon the reverse primer annealing to the treated DNA, said guanine will either form a base pair with an abnormally methylated cytosine, the presence of which is indicative of prostate cancer, or will form a mismatch with uracil, which is not indicative of prostate cancer.

7. The method of claim 6, wherein said PCR amplification uses a forward primer having cytosine at at least one site corresponding to an abnormally methylated cytosine, the presence of which is indicative of prostate cancer.

8. The method of claim 7, wherein the forward and reverse primers are of 12 to 30 nucleotides in length.

9. The method of claim 8, wherein the forward and reverse primers are selected so as to anneal to a sequence within the target region that includes two to four abnormally methylated cytosines, the presence of which are indicative of prostate cancer.

10. The method of claim 4, wherein the treatment of DNA obtained from a tissue or body fluid sample of the subject involves reacting the DNA with bisulphite.

11. The method of claim 7, wherein the amplification involves PCR amplification using primer pairs consisting of a forward and a reverse primer selected from each of the following groups:
    Forward Primers
    CGCGAGGTTTTCGTTGGAGTTTCGTCGTC (SEQ ID NO: 1)
    CGTTATTAGTGAGTACGCGCGGTTC (SEQ ID NO: 2)

TTTTTAGGGGGTTYGGAGCGTTTC (SEQ ID NO: 6)
GGTAGGTTGYGTTTATCGC (SEQ ID NO: 7)
Reverse Primers
TCCCATCCCTCCCCGAAACGCTCCG (SEQ ID NO: 8)
GAAACGCTCCGAACCCCTAAAAACCGCTAACG (SEQ ID NO: 9)
AAAAATTCRAATCTCTCCGAATAAACG (SEQ ID NO: 15)
AAAAACCRAAATAAAAACCACACGACG (SEQ ID NO: 16),
wherein Y is C, T, or a mixture thereof; and R is A, G, or a mixture thereof.

12. The method of claim 7, wherein the amplification step involves PCR amplification using primer pairs consisting of a forward and a reverse primer selected from each of the following groups:
Forward Primers
CGCGAGGTTTTCGTTGGAGTTTCGTCGTC (SEQ ID NO: 1)
CGTTATTAGTGAGTACGCGCGGTTC (SEQ ID NO: 2)
Reverse Primers
TCCCATCCCTCCCCGAAACGCTCCG (SEQ ID NO: 8)
GAAACGCTCCGAACCCCTAAAAACCGCTAACG (SEQ ID NO: 9).

13. The method of claim 7, wherein the amplification step involves PCR amplification using primer pairs consisting of a forward and a reverse primer selected from each of the following groups:
Forward Primers
TTTTTAGGGGGTTYGGAGCGTTTC (SEQ ID NO: 6)
GGTAGGTTGYGTTTATCGC (SEQ ID NO: 7)
Reverse Primers
AAAAATTCRAATCTCTCCGAATAAACG (SEQ ID NO: 15)
AAAAACCRAAATAAAAACCACACGACG (SEQ ID NO: 16),
wherein Y is C, T, or a mixture thereof; and R is A, G, or a mixture thereof.

14. The method of claim 1, wherein said tissue or body fluid sample is blood, blood serum, blood plasma, urine, lymph, or bone marrow.

15. The method of claim 1, wherein said detecting comprises the steps of:
(i) treating DNA, obtained from a tissue or body fluid sample of said subject, with a restriction endonuclease that recognizes a restriction site within a glutathione S-transferase (GST) Pi gene and which does not cleave at said restriction site when a cytosine in said restriction site is methylated; wherein said abnormally methylated cytosine is within said restriction site; and wherein said DNA comprises a GST-Pi gene;
(ii) carrying out an amplification reaction of a target region of the GST-Pi gene using the resulting treated DNA of step (i) as a template, wherein said target region contains said restriction site and is amplified only when said restriction site has not been cleaved in step (i) by said restriction endonuclease;
(iii) determining if said target region is amplified in step (ii), wherein amplification of the target region is indicative of abnormal methylation of said cytosine in said sample, to thereby diagnose said prostate cancer.

16. The method of claim 15, wherein said amplification reaction involves polymerase chain reaction (PCR) amplification.

17. A method for diagnosing liver cancer in a subject suspected of having liver cancer, comprising:
detecting, in a tissue or body fluid sample from said subject, the presence of an abnormally methylated cytosine in the glutathione S-transferase (GST) Pi gene, wherein the presence of said abnormally methylated cytosine is indicative of liver cancer; and
wherein said abnormally methylated cytosine is within a CpG site located within a region defined by and including nucleotides 1232 to 1942 (CpG sites +1 to +55) of SEQ ID NO: 60.

18. The method of claim 17, wherein said abnormally methylated cytosine is within a CpG site located within a region defined by and including nucleotides 1273 to 1942 (CpG sites +9 to +55) of SEQ ID NO: 60.

19. The method of claim 17, wherein the presence of at least two abnormally methylated cytosines are detected, the presence of which are indicative of liver cancer.

20. The method of claim 17, wherein said detecting comprises the steps of:
(i) treating DNA, obtained from a tissue or body fluid sample of said subject, so that unmethylated cytosines in the DNA are converted to uracil or another nucleotide capable of forming a base pair with adenine, while methylated cytosines in the DNA are left unchanged or are converted to a nucleotide capable of forming a base pair with guanine, wherein said DNA comprises said glutathione S-transferase (GST) Pi gene;
(ii) carrying out an amplification reaction of a target region within said GST-Pi gene using the resulting treated DNA of step (i) as a template, wherein said target region is amplified only when said abnormally methylated cytosine is left unchanged or is converted to a nucleotide capable of forming a base pair with guanine as a result of said treating in step (i), and
(iii) determining if said target region is amplified in step (ii), wherein amplification of the target region is indicative of the presence of said abnormally methylated cytosine in said sample, thereby diagnosing said liver cancer.

21. The method of claim 20, wherein said amplification reaction involves polymerase chain reaction (PCR) amplification.

22. The method of claim 21, wherein said PCR amplification reaction uses a reverse primer having guanine at at least one site whereby, upon the reverse primer annealing to the treated DNA, said guanine will either form a base pair with a methylated cytosine, the presence of which is indicative of liver cancer, or will form a mismatch with uracil, which is not indicative of liver cancer.

23. The method of claim 22, wherein said PCR amplification uses a forward primer having cytosine at at least one site corresponding to an abnormally methylated cytosine, the presence of which is indicative of liver cancer.

24. The method of claim 23, wherein the forward and reverse primers are of 12 to 30 nucleotides in length.

25. The method of claim 24, wherein the forward and reverse primers are selected so as to anneal to a sequence within the target region that includes two to four abnormally methylated cytosines, the presence of which are indicative of liver cancer.

26. The method of claim 20, wherein the treatment of DNA obtained from a tissue or body fluid sample of the subject involves reacting the DNA with bisulphite.

27. The method of claim 17, wherein said tissue or body fluid sample is blood, blood serum, blood plasma, urine, lymph, or bone marrow.

28. The method of claim 23, wherein the amplification involves PCR amplification using primer pairs consisting of a forward and a reverse primer selected from each of the following groups:
Forward Primers
CGCGAGGTTTTCGTTGGAGTTTCGTCGTC (SEQ ID NO: 1)
CGTTATTAGTGAGTACGCGCGGTTC (SEQ ID NO: 2)
TTTTTAGGGGGTTYGGAGCGTTTC (SEQ ID NO: 6)
GGTAGGTTGYGTTTATCGC (SEQ ID NO: 7)
Reverse Primers
TCCCATCCCTCCCCGAAACGCTCCG (SEQ ID NO: 8)
GAAACGCTCCGAACCCCCTAAAAACCGCTAACG (SEQ ID NO: 9)
AAAAATTCRAATCTCTCCGAATAAACG (SEQ ID NO: 15)
AAAAACCRAAATAAAAACCACACGACG (SEQ ID NO: 16),
wherein Y is C, T, or a mixture thereof, and R is A, G, or a mixture thereof.

29. The method of claim 23, wherein the amplification step involves PCR amplification using primer pairs consisting of a forward and a reverse primer selected from each of the following groups:
Forward Primers
CGCGAGGTTTTCGTTGGAGTTTCGTCGTC (SEQ ID NO: 1)
CGTTATTAGTGAGTACGCGCGGTTC (SEQ ID NO: 2)
Reverse Primers
TCCCATCCCTCCCCGAAACGCTCCG (SEQ ID NO: 8)
GAAACGCTCCGAACCCCCTAAAAACCGCTAACG (SEQ ID NO: 9).

30. The method of claim 23, wherein the amplification step involves PCR amplification using primer pairs consisting of a forward and a reverse primer selected from each of the following groups:
Forward Primers
TTTTTAGGGGGTTYGGAGCGTTTC (SEQ ID NO: 6)
GGTAGGTTGYGTTTATCGC (SEQ ID NO: 7)
Reverse Primers
AAAAATTCRAATCTCTCCGAATAAACG (SEQ ID NO: 15)
AAAAACCRAAATAAAAACCACACGACG (SEQ ID NO: 16),
wherein Y is C, T, or a mixture thereof; and R is A, G, or a mixture thereof.

31. The method of claim 17, wherein said detecting comprises the steps of:
(i) treating DNA, obtained from a tissue or body fluid sample of said subject, with a restriction endonuclease that recognizes a restriction site within a glutathione S-transferase (GST) Pi gene and which does not cleave at said restriction site when a cytosine in said restriction site is methylated; wherein said abnormally methylated cytosine is within said restriction site; and wherein said DNA comprises a GST-Pi gene;
(ii) carrying out an amplification reaction of a target region of the GST-Pi gene using the resulting treated DNA of step (i) as a template, wherein said target region contains said restriction site and is amplified only when said restriction site has not been cleaved in step (i) by said restriction endonuclease;
(iii) determining if said target region is amplified in step (ii), wherein amplification of the target region is indicative of abnormal methylation of said cytosine in said sample, to thereby diagnose said liver cancer.

32. The method of claim 31, wherein said amplification reaction involves polymerase chain reaction (PCR) amplification.

33. A method for diagnosing prostate cancer or liver cancer in a subject, comprising:
detecting, in a tissue or body fluid sample from said subject, the presence of an abnormally methylated cytosine in the glutathione S-transferase (GST) Pi gene, wherein the presence of said abnormally methylated cytosine is indicative of prostate cancer or liver cancer; and
wherein said abnormally methylated cytosine is within a CpG site located within a region defined by and including nucleotides 1232 to 1942 (CpG sites +1 to +55) of SEQ ID NO: 60.

* * * * *

UNITED STATES PATENT AND TRADEMARK OFFICE
CERTIFICATE OF CORRECTION

| | |
|---|---|
| PATENT NO. | : 7,049,062 B2 |
| APPLICATION NO. | : 09/673448 |
| DATED | : May 23, 2006 |
| INVENTOR(S) | : Susan J. Clark, Douglas S. Millar and Peter L. Molloy |

It is certified that error appears in the above-identified patent and that said Letters Patent is hereby corrected as shown below:

Table 3 omitted in patent. Please insert the attached Table 3 between column 24 last line and column 25, first line.

Signed and Sealed this

Twentieth Day of January, 2009

JON W. DUDAS
*Director of the United States Patent and Trademark Office*

TABLE 3

| Primer | Forward or Reverse | Primer Sequence (5'-3') | Co-ordinates | CpG sites |
|---|---|---|---|---|
| CGPS-1 | F | CGGCGAGGTTTTCGTTGGAGTTTCGTCGTC (SEQ ID NO: 1) | 1210-1238 | -3 to +3 |
| CGPS-2 | F | GGTTATTAGTGAGTAGGCGCGGTTC (SEQ ID NO: 2) | 1247-1271 | +4 to +8 |
| CGPS-3 | R | TCCCATCCCTCCCGAAACGCTCCG (SEQ ID NO: 8) | 1428-1452 | +21 to +23 |
| CGPS-4 | R | GAAACGCTCCGAACCCCTAAAAACCGCTAACG (SEQ ID NO: 9) | 1406-1438 | +19 to +23 |
| CGPS-5 | F | YGGTTTTAGGGAATTTTTTTTCGC (SEQ ID NO: 3) | 894-917 | -39 to -37 |
| CGPS-6 | F | YGGYGYGYGTTAGTTYGTTGYGTATATTTC (SEQ ID NO: 4) | 925-952 | -36 to -31 |
| CGPS-11 | F | GGGAATTTTTTCGGATGTTYGGCGC (SEQ ID NO: 5) | 902-930 | -38 to -34 |
| CGPS-7 | R | CRCCCTAAAATCCCCRAAATCRCCGCG (SEQ ID NO: 10) | 1038-1064 | -23 to -27 |
| CGPS-8 | R | ACCCCRACRCCRCTACACCCCRAAGTCG (SEQ ID NO: 11) | 1077-1104 | -16 to -21 |
| CGPS-9 | R | CTCTTCTAAAATCCCCRCRAACTCCCGCCG (SEQ ID NO: 12) | 1113-1143 | -12 to -15 |
| CGPS-12 | R | AAAACRCCCTAAAATCCCCGAAATCGCCG (SEQ ID NO: 13) | 1040-1068 | -23 to -26 |
| CGPS-13 | R | AACTCCCRCCGACCCAACCCGACGACCG (SEQ ID NO: 14) | 1094-1123 | -14 to -18 |
| CGPS-21 | F | TTTTTAGGGGGTTYGGAGGGTTC (SEQ ID NO: 6) | 1415-1438 | +21 to +23 |
| CGPS-22 | F | GGTAGGTTGYGTTTATCGC (SEQ ID NO: 7) | 1473-1491 | +26 to +28 |
| CGPS-23 | R | AAAAATTCRAATCTCTCCGAATAAACG (SEQ ID NO: 15) | 1640-1666 | +36 to +34 |
| CGPS-24 | R | AAAAACCRAATAAAAACCACACGACG (SEQ ID NO: 16) | 1676-1703 | +39 to +37 |

SEQUENCE LISTING

<160> NUMBER OF SEQ ID NOS: 60

<210> SEQ ID NO 1
<211> LENGTH: 29
<212> TYPE: DNA
<213> ORGANISM: Homosapiens

<400> SEQUENCE: 1
cgcgaggttt tcgttggagt ttcgtcgtc                                    29

<210> SEQ ID NO 2
<211> LENGTH: 25
<212> TYPE: DNA
<213> ORGANISM: Homo sapiens

<400> SEQUENCE: 2
cgttattagt gagtacgcgc ggttc                                        25

<210> SEQ ID NO 3
<211> LENGTH: 24
<212> TYPE: DNA
<213> ORGANISM: Homo sapiens

<400> SEQUENCE: 3
yggttttagg gaattttttt tcgc                                         24

<210> SEQ ID NO 4
<211> LENGTH: 28
<212> TYPE: DNA
<213> ORGANISM: Homo sapiens

<400> SEQUENCE: 4
yggygygtta gttygttgyg tatatttc                                     28

<210> SEQ ID NO 5
<211> LENGTH: 29
<212> TYPE: DNA
<213> ORGANISM: Homo sapiens

<400> SEQUENCE: 5
gggaattttt tttcgcgatg tttyggcgc                                    29

<210> SEQ ID NO 6
<211> LENGTH: 24
<212> TYPE: DNA
<213> ORGANISM: Homo sapiens

<400> SEQUENCE: 6

```
tttttagggg gttyggagcg tttc                                          24

<210> SEQ ID NO 7
<211> LENGTH: 19
<212> TYPE: DNA
<213> ORGANISM: Homo sapiens

<400> SEQUENCE: 7
ggtaggttgy gtttatcgc                                                19

<210> SEQ ID NO 8
<211> LENGTH: 27
<212> TYPE: DNA
<213> ORGANISM: Homosapiens

<400> SEQUENCE: 8
aaaaattcra atctctccga ataaacg                                       27

<210> SEQ ID NO 9
<211> LENGTH: 27
<212> TYPE: DNA
<213> ORGANISM: Homosapiens

<400> SEQUENCE: 9
aaaaaccraa ataaaaacca cacgacg                                       27

<210> SEQ ID NO 10
<211> LENGTH: 25
<212> TYPE: DNA
<213> ORGANISM: Homo sapiens

<400> SEQUENCE: 10
tcccatccct ccccgaaacg ctccg                                         25

<210> SEQ ID NO 11
<211> LENGTH: 33
<212> TYPE: DNA
<213> ORGANISM: Homosapiens

<400> SEQUENCE: 11
gaaacgctcc gaaccccta aaaccgcta acg                                  33

<210> SEQ ID NO 12
<211> LENGTH: 27
<212> TYPE: DNA
<213> ORGANISM: Homo sapiens

<400> SEQUENCE: 12
crccctaaaa tcccraaat crccgcg                                        27

<210> SEQ ID NO 13
<211> LENGTH: 30
<212> TYPE: DNA
<213> ORGANISM: Homo sapiens

<400> SEQUENCE: 13
accccracra ccrctacacc ccraacgtcg                                    30

<210> SEQ ID NO 14
<211> LENGTH: 31
<212> TYPE: DNA
<213> ORGANISM: Homo sapiens
```

<400> SEQUENCE: 14
ctcttctaaa aaatcccrcr aactcccgcc g					31

<210> SEQ ID NO 15
<211> LENGTH: 29
<212> TYPE: DNA
<213> ORGANISM: Homo sapiens

<400> SEQUENCE: 15
aaaacrccct aaaatccccg aaatcgccg						29

<210> SEQ ID NO 16
<211> LENGTH: 30
<212> TYPE: DNA
<213> ORGANISM: Homo sapiens

<400> SEQUENCE: 16
aactcccrcc gaccccaacc ccgacgaccg					30

<210> SEQ ID NO 17
<211> LENGTH: 23
<212> TYPE: DNA
<213> ORGANISM: Artificial Sequence
<220> FEATURE:
<223> OTHER INFORMATION: Oligo which binds bisulfite-converted human
    GST-Pi gene

<400> SEQUENCE: 17
aaacctaaaa aataaacaaa caa						23

<210> SEQ ID NO 18
<211> LENGTH: 23
<212> TYPE: DNA
<213> ORGANISM: Artificial Sequence
<220> FEATURE:
<223> OTHER INFORMATION: Oligo whcih binds non-converted human GST-Pi
    gene

<400> SEQUENCE: 18
gggcctaggg agtaaacaga cag						23

<210> SEQ ID NO 19
<211> LENGTH: 25
<212> TYPE: DNA
<213> ORGANISM: Artificial Sequence
<220> FEATURE:
<223> OTHER INFORMATION: Oligo which binds human GST-Pi gene

<400> SEQUENCE: 19
cctttccctc tttcccarrt cccca						25

<210> SEQ ID NO 20
<211> LENGTH: 25
<212> TYPE: DNA
<213> ORGANISM: Artificial Sequence
<220> FEATURE:
<223> OTHER INFORMATION: Oligo which binds bisulfite-converted human
    GST-Pi gene

<400> SEQUENCE: 20
tttggtattt tttttcgggt tttag						25

<210> SEQ ID NO 21
<211> LENGTH: 25
<212> TYPE: DNA

```
<213> ORGANISM: Artificial Sequence
<220> FEATURE:
<223> OTHER INFORMATION: Oligo which binds non-converted human GST-Pi
      gene

<400> SEQUENCE: 21
cttggcatcc tcccccgggc tccag                                              25

<210> SEQ ID NO 22
<211> LENGTH: 26
<212> TYPE: DNA
<213> ORGANISM: Artificial Sequence
<220> FEATURE:
<223> OTHER INFORMATION: Oligo which binds human GST-Pi gene

<400> SEQUENCE: 22
ggyagggaag ggaggyaggg gytggg                                             26

<210> SEQ ID NO 23
<211> LENGTH: 31
<212> TYPE: DNA
<213> ORGANISM: Homo sapiens

<400> SEQUENCE: 23
ttatgtaata aatttgtata ttttgtatat g                                       31

<210> SEQ ID NO 24
<211> LENGTH: 25
<212> TYPE: DNA
<213> ORGANISM: Homo sapiens

<400> SEQUENCE: 24
tgtagattat ttaaggttag gagtt                                              25

<210> SEQ ID NO 25
<211> LENGTH: 27
<212> TYPE: DNA
<213> ORGANISM: Homo sapiens

<400> SEQUENCE: 25
aaacctaaaa aataaacaaa caacaaa                                            27

<210> SEQ ID NO 26
<211> LENGTH: 29
<212> TYPE: DNA
<213> ORGANISM: Homosapiens

<400> SEQUENCE: 26
aaaaaacctt tccctctttc ccaaatccc                                          29

<210> SEQ ID NO 27
<211> LENGTH: 27
<212> TYPE: DNA
<213> ORGANISM: Homo sapiens

<400> SEQUENCE: 27
tttgttgttt gtttatttt taggttt                                             27

<210> SEQ ID NO 28
<211> LENGTH: 26
<212> TYPE: DNA
<213> ORGANISM: Homo sapiens

<400> SEQUENCE: 28
```

```
gggatttggg aaagagggaa aggttt                                          26
```

<210> SEQ ID NO 29
<211> LENGTH: 24
<212> TYPE: DNA
<213> ORGANISM: Homosapiens

<400> SEQUENCE: 29

```
actaaaaact ctaaacccca tccc                                            24
```

<210> SEQ ID NO 30
<211> LENGTH: 24
<212> TYPE: DNA
<213> ORGANISM: Homo sapiens

<400> SEQUENCE: 30

```
aacctaatac taccttaacc ccat                                            24
```

<210> SEQ ID NO 31
<211> LENGTH: 33
<212> TYPE: DNA
<213> ORGANISM: Homo sapiens

<400> SEQUENCE: 31

```
aatcctcttc ctactatcta tttactccct aaa                                  33
```

<210> SEQ ID NO 32
<211> LENGTH: 29
<212> TYPE: DNA
<213> ORGANISM: Homo sapiens

<400> SEQUENCE: 32

```
aaaacctaaa aaaaaaaaaa aaacttccc                                       29
```

<210> SEQ ID NO 33
<211> LENGTH: 29
<212> TYPE: DNA
<213> ORGANISM: Homo sapiens

<400> SEQUENCE: 33

```
ttggttttat gttgggagtt ttgagtttt                                       29
```

<210> SEQ ID NO 34
<211> LENGTH: 29
<212> TYPE: DNA
<213> ORGANISM: Homo sapiens

<400> SEQUENCE: 34

```
ttttgtgggg agttggggtt tgatgttgt                                       29
```

<210> SEQ ID NO 35
<211> LENGTH: 29
<212> TYPE: DNA
<213> ORGANISM: Homo sapiens

<400> SEQUENCE: 35

```
ggtttagagt ttttagtatg gggttaatt                                       29
```

<210> SEQ ID NO 36
<211> LENGTH: 20
<212> TYPE: DNA
<213> ORGANISM: Homo sapiens

<400> SEQUENCE: 36

```
<210> SEQ ID NO 37
<211> LENGTH: 29
<212> TYPE: DNA
<213> ORGANISM: Homo sapiens

<400> SEQUENCE: 37
aactctaacc ctaatctacc aacaacata                              29

<210> SEQ ID NO 38
<211> LENGTH: 29
<212> TYPE: DNA
<213> ORGANISM: Homo sapiens

<400> SEQUENCE: 38
caaaaaactt taaataaacc ctcctacca                              29

<210> SEQ ID NO 39
<211> LENGTH: 32
<212> TYPE: DNA
<213> ORGANISM: Homo sapiens

<400> SEQUENCE: 39
gttttgtggt taggttgttt tttaggtgtt ag                          32

<210> SEQ ID NO 40
<211> LENGTH: 30
<212> TYPE: DNA
<213> ORGANISM: Homo sapiens

<400> SEQUENCE: 40
gttttgagta tttgttgtgt ggtagttttt                             30

<210> SEQ ID NO 41
<211> LENGTH: 30
<212> TYPE: DNA
<213> ORGANISM: Homo sapiens

<400> SEQUENCE: 41
ttaatataaa taaaaaaaat atatttacaa                             30

<210> SEQ ID NO 42
<211> LENGTH: 34
<212> TYPE: DNA
<213> ORGANISM: Homo sapiens

<400> SEQUENCE: 42 caaccccaa tacccaaccc taatacaaat actc                         34

<210> SEQ ID NO 43
<211> LENGTH: 26
<212> TYPE: DNA
<213> ORGANISM: Homo sapiens

<400> SEQUENCE: 43
ggttttagtt tttggttgtt tggatg                                 26

<210> SEQ ID NO 44
<211> LENGTH: 26
<212> TYPE: DNA
<213> ORGANISM: Homo sapiens
```
tagtattagg ttagggtttt                                        20

-continued

```
<400> SEQUENCE: 44
tttttttgtt tttagtatat gtgggg                                26

<210> SEQ ID NO 45
<211> LENGTH: 30
<212> TYPE: DNA
<213> ORGANISM: Homosapiens

<400> SEQUENCE: 45
atactaaaaa aactattttc taatcctcta                            30

<210> SEQ ID NO 46
<211> LENGTH: 29
<212> TYPE: DNA
<213> ORGANISM: Homosapiens

<400> SEQUENCE: 46
ccaaactaaa aactccaaaa aaccactaa                             29

<210> SEQ ID NO 47
<211> LENGTH: 38
<212> TYPE: DNA
<213> ORGANISM: Artificial Sequence
<220> FEATURE:
<223> OTHER INFORMATION: M13-human GST-Pi oligonucleotide

<400> SEQUENCE: 47
tgtaaaacga cggccagtgg gatttgggaa agagggaa                   38

<210> SEQ ID NO 48
<211> LENGTH: 38
<212> TYPE: DNA
<213> ORGANISM: Artificial Sequence
<220> FEATURE:
<223> OTHER INFORMATION: M13-human GST-Pi oligonucleotide

<400> SEQUENCE: 48
tgtaaaacga cggccagttg ttgggagttt tgagtttt                   38

<210> SEQ ID NO 49
<211> LENGTH: 31
<212> TYPE: DNA
<213> ORGANISM: Artificial Sequence
<220> FEATURE:
<223> OTHER INFORMATION: M13-human GST-Pi oligonucleotide

<400> SEQUENCE: 49
tgtaaaacga cggccagtta gtattaggtt a                          31

<210> SEQ ID NO 50
<211> LENGTH: 37
<212> TYPE: DNA
<213> ORGANISM: Artificial Sequence
<220> FEATURE:
<223> OTHER INFORMATION: M13-human GST-Pi oligonucleotide

<400> SEQUENCE: 50
tgtaaaacga cggccagtgt tttgagtatt tgttgtg                    37

<210> SEQ ID NO 51
<211> LENGTH: 35
<212> TYPE: DNA
<213> ORGANISM: Artificial Sequence
<220> FEATURE:
<223> OTHER INFORMATION: M13-human GST-Pi oligonucleotide
```

<400> SEQUENCE: 51

| tgtaaaacga cggccagtgt ttttagtata tgtgg | 35 |

<210> SEQ ID NO 52
<211> LENGTH: 499
<212> TYPE: DNA
<213> ORGANISM: Homo sapiens

<400> SEQUENCE: 52

| tgcagatcac ctaaggtcag gagttcgaga ccagcccggc caacatggtg aaacccgtc | 60 |
| tctactaaaa atacaaaaat cagccagatg tggcacgcac ctataattcc acctactcgg | 120 |
| gaggctgaag cagaattgct tgaacccgag aggcggaggt tgcagtgagc cgccgagatc | 180 |
| gcgccactgc actccagcct gggccacagc gtgagactac gtcataaaat aaaataaaat | 240 |
| aacacaaaat aaataaaat aaaataaaat aaaataaaat aataaaataa aataaaataa | 300 |
| aataaaataa aataaaataa agcaatttcc tttcctctaa gcggcctcca ccctctccc | 360 |
| ctgccctgtg aagcgggtgt gcaagctccg ggatcgcagc ggtcttaggg aatttccccc | 420 |
| cgcgatgtcc cggcgcgcca gttcgctgcg cacacttcgc tgcggtcctc ttcctgctgt | 480 |
| ctgtttactc cctaggccc | 499 |

<210> SEQ ID NO 53
<211> LENGTH: 316
<212> TYPE: DNA
<213> ORGANISM: Homo sapiens

<400> SEQUENCE: 53

| gggacctggg aaagagggaa aggcttcccc ggccagctgc gcggcgactc cggggactcc | 60 |
| agggcgcccc tctgcggccg acgcccgggg tgcagcggcc gccggggctg gggccggcgg | 120 |
| gagtccgcgg gaccctccag aagagcggcc ggcgccgtga ctcagcactg gggcggagcg | 180 |
| ggcggggacc acccttataa ggctcggagg ccgcgaggcc ttcgctggag tttcgccgcc | 240 |
| gcagtcttcg ccaccagtga gtacgcgcgg cccgcgtccc cggggatggg gctcagagct | 300 |
| cccagcatgg ggccaa | 316 |

<210> SEQ ID NO 54
<211> LENGTH: 603
<212> TYPE: DNA
<213> ORGANISM: Homo sapiens

<400> SEQUENCE: 54

| cagcatcagg cccgggctcc cggcagggct cctcgcccac ctcgagaccc gggacggggg | 60 |
| cctaggggac ccaggacgtc cccagtgccg ttagcggctt tcaggggggcc cggagcgcct | 120 |
| cggggaggga tgggaccccg ggggcgggga gggggggcag gctgcgctca ccgcgccttg | 180 |
| gcatcctccc ccgggctcca gcaaactttt ctttgttcgc tgcagtgccg ccctacaccg | 240 |
| tggtctattt cccagttcga ggtaggagca tgtgtctggc agggaaggga ggcaggggct | 300 |
| ggggctgcag cccacagccc ctcgcccacc ggagagatc cgaacccccct tatccctccg | 360 |
| tcgtgtggct tttaccccgg gcctccttcc tgttcccgc ctctcccgcc atgcctgctc | 420 |
| ccgccccag tgttgtgtga atcttcgga ggaacctgtt tacctgttcc ctccctgcac | 480 |
| tcctgaccc tccccgggtt gctgcgaggc ggagtcggcc cggtcccac atctcgtact | 540 |
| tctccctccc cgcaggccgc tgcgcggccc tgcgcatgct gctggcagat cagggccaga | 600 | gct 603

<210> SEQ ID NO 55
<211> LENGTH: 266
<212> TYPE: DNA
<213> ORGANISM: Homo sapiens

<400> SEQUENCE: 55

| gctctgagca cctgctgtgt ggcagtctct catccttcca cgcacatcct cttcccctcc | 60 |
| tcccaggctg gggctcacag acagcccct ggttggccca tccccagtga ctgtgtgttg | 120 |
| atcaggcgcc cagtcacgcg gcctgctccc ctccacccaa ccccagggct ctatgggaag | 180 |
| gaccagcagg aggcagccct ggtggacatg gtgaatgacg gcgtggagga cctccgctgc | 240 |
| aaatacatct ccctcatcta caccaa | 266 |

<210> SEQ ID NO 56
<211> LENGTH: 287
<212> TYPE: DNA
<213> ORGANISM: Homo sapiens

<400> SEQUENCE: 56

| tcccctgct ctcagcatat gtgggcgcc tcagtgcccg gcccaagctc aaggccttcc | 60 |
| tggcctcccc tgagtacgtg aacctcccca tcaatgcaa cggaaacag tgagggttgg | 120 |
| ggggactctg agcgggaggc agagtttgcc ttcctttctc caggaccaat aaaatttcta | 180 |
| agagagctac tatgagcact gtgtttcctg ggacggggct tagggttcct cagcctcgag | 240 |
| gtcggtggga gggcagagca gaggactaga aaacagctcc tccagca | 287 |

<210> SEQ ID NO 57
<211> LENGTH: 524
<212> TYPE: DNA
<213> ORGANISM: Homo sapiens

<400> SEQUENCE: 57

| ataaaataaa ataaaataaa ataaagcaat ttcctttcct ctaagcggcc tccaccccctc | 60 |
| tcccctgccc tgtgaagcgg gtgtgcaagc tccgggatcg cagcggtctt agggaatttc | 120 |
| ccccgcgat gtcccggcgc gccagttcgc tgcgcacact tcgctgcggt cctcttcctg | 180 |
| ctgtctgttt actccctagg ccccgctggg gacctggaa agagggaaag gcttcccgg | 240 |
| ccagctgcgc ggcgactccg gggactccag ggcgcccctc tgcggccgac gcccggggtg | 300 |
| cagcggccgc cgggctggg gccggcggga gtccgcggga ccctccagaa gagcggccgg | 360 |
| cgccgtgact cagcactggg gcggagcggg gcgggaccac ccttataagg ctcggaggcc | 420 |
| gcgaggcctt cgctggagtt tcgccgccgc agtcttcgcc accagtgagt acgcgcggcc | 480 |
| cgcgtccccg gggatggggc tcagagctcc cagcatgggg ccaa | 524 |

<210> SEQ ID NO 58
<211> LENGTH: 524
<212> TYPE: DNA
<213> ORGANISM: Homo sapiens

<400> SEQUENCE: 58

| ataaaataaa ataaaataaa ataaagtaat tttttttttt ttaagtggtt tttatttttt | 60 |
| tttttgttt tgtgaagtgg gtgtgtaagt tttgggattg tagtggtttt agggaatttt | 120 |
| tttttgtgat gttttggtgt gttagtttgt tgtgtatatt ttgttgtggt tttttttttg | 180 |
| ttgtttgttt atttttagg ttttgttggg gatttgggaa agagggaaag gttttttttgg | 240 |

```
ttagttgtgt ggtgattttg gggattttag ggtgttttt tgtggttgat gtttggggtg      300
tagtggttgt tggggttggg gttggtggga gtttgtggga ttttttagaa gagtggttgg      360
tgttgtgatt tagtattggg gtggagtggg gtgggattat ttttataagg tttggaggtt      420
gtgaggtttt tgttggagtt ttgttgttgt agttttttgtt attagtgagt atgtgtggtt      480
tgtgtttttg gggatggggt ttagagtttt tagtatgggg ttaa                      524

<210> SEQ ID NO 59
<211> LENGTH: 524
<212> TYPE: DNA
<213> ORGANISM: Homo sapiens

<400> SEQUENCE: 59
ataaaataaa ataaaataaa ataaagtaat tttttttttt ttaagcggtt tttattttt       60 ttttttgttt tgtgaagcgg gtgtgtaagt ttcgggatcg tagcggtttt agggaatttt      120
ttttcgcgat gtttcggcgc gttagttcgt tgcgtatatt tcgttgcggt ttttttttg       180 ttgtttgttt attttttagg tttcgttggg gatttgggaa agaggggaag gttttttcgg      240
ttagttgcgc ggcgatttcg gggattttag ggcgttttt tgcggtcgac gttcggggtg      300
tagcggtcgt cggggttggg gtcggcggga gttcgcggga tttttagaa gagcggtcgg      360 cgtcgtgatt tagtattggg gcggagcggg gcgggattat ttttataagg ttcggaggtc      420
gcgaggtttt cgttggagtt tcgtcgtcgt agttttcgtt attagtgagt acgcgcggtt      480
cgcgttttcg gggatggggt ttagagtttt tagtatgggg ttaa                      524

<210> SEQ ID NO 60
<211> LENGTH: 4262
<212> TYPE: DNA
<213> ORGANISM: Homo sapiens

<400> SEQUENCE: 60
aacaagagat caatatctag aataaatgga gatctgcaaa tcaacagaaa gtaggcagca       60
aagccaaaga aaatagccta aggcacagcc actaaaagga acgtgatcat gtccttttgca     120 gggacatggg tggagctgga agccgttagc ctcagcaaac tcacacagga acagaaaacc      180
agcgagaccg catggtctca cttataagtg ggagctgaac aatgagaaca catggtcaca      240 tgcggcgat caacacacac tggtgcctgt tgagcggggt gctggggagg agagtacca       300 ggaagaatag ctaagggata ctgggcttaa tacctgggtg atgggatgat ctgtacagca      360
aaccatcatg gcgcacacac ctatgtaaca aacctgcaca tcctgcacat gtaccccaga      420
acttcaaata aaagttggac ggccaggcgt ggtggctcac gcctgtaatc ccagcacttt      480
gggaagccga ggcgtgcaga tcacctaagg tcaggagttc gagaccagcc cggccaacat      540
ggtgaaaccc cgtctctact aaaaatacaa aaatcagcca gatgtggcac gcacctataa      600
ttccacctac tcgggaggct gaagcagaat tgcttgaacc cgagaggcgg aggttgcagt      660
gagccgccga gatcgcgcca ctgcactcca gcctgggcca cagcgtgaga ctacgtcata      720
aaataaaata aaataacaca aaataaaata aaataaaata aaataaaata aaataataaa      780
ataaaataaa ataaaataaa ataaaataaa ataaagcaat tccttttcct ctaagcggcc     840
tccacccctc tcccctgccc tgtgaagcgg gtgtgcaagc tccgggatcg cagcggtctt      900
agggaatttc ccccgcgat gtcccggcgc gccagttcgc tgcgcacact tcgctgcggt      960
cctcttcctg ctgtctgttt actccctagg ccccgctggg gacctgggaa agagggaaag     1020
```

-continued

```
gcttccccgg ccagctgcgc ggcgactccg gggactccag ggcgcccctc tgcggccgac      1080 gcccgggtg cagcggccgc cggggctggg gccggcggga gtccgcggga ccctccagaa       1140
gagcggccgc cgccgtgact cagcactggg gcggagcggg gcgggaccac ccttataagg      1200
ctcggaggcc gcgaggcctt cgctggagtt tcgccgccgc agtcttcgcc accagtgagt     1260
acgcgcggcc cgcgtccccg gggatggggc tcagagctcc cagcatgggg ccaacccgca      1320
gcatcaggcc cgggctcccg gcagggctcc tcgcccacct cgagacccgg gacggggcc      1380 tagggaccc aggacgtccc cagtgccgtt agcggctttc aggggcccg gagcgcctcg       1440 gggagggatg ggaccccggg ggcggggagg ggggcaggc tgcgctcacc gcgccttggc      1500
atcctccccc gggctccagc aaacttttct ttgttcgctg cagtgccgcc ctacaccgtg     1560
gtctatttcc cagttcgagg taggagcatg tgtctggcag ggaagggagg cagggctgg      1620 ggctgcagcc cacagcccct cgcccacccg gagagatccg aaccccctta tccctccgtc    1680
gtgtggcttt taccccgggc ctccttcctg ttccccgcct ctcccgccat gcctgctccc    1740
cgccccagtg ttgtgtgaaa tcttcggagg aacctgttta cctgttccct ccctgcactc    1800 ctgaccctc cccgggttgc tgcgaggcgg agtcggcccg gtccccacat ctcgtacttc      1860
tccctccccg caggccgctg cgcggccctg cgcatgctgc tggcagatca gggccagagc    1920
tggaaggagg aggtggtgac cgtggagacg tggcaggagg gctcactcaa agcctcctgc    1980
gtaagtgacc atgcccgggc aaggggaggg ggtgctgggc cttaggggc tgtgactagg     2040 atcggggac gccaagctc agtgcccctc cctgagccat gcctccccca acagctatac     2100
gggcagctcc ccaagttcca ggacggagac ctcaccctgt accagtccaa taccatcctg   2160
cgtcacctgg gccgcaccct tggtgagtct tgaacctcca agtccagggc aggcatgggc    2220
aagcctctgc ccccggagcc cttttgttta aatcagctgc cccgcagccc tctggagtgg    2280
aggaaactga gacccactga ggttacgtag tttgcccaag gtcaagcctg ggtgcctgca     2340
atccttgccc tgtgccaggc tgcctcccag gtgtcaggtg agctctgagc acctgctgtg   2400
tggcagtctc tcatccttcc acgcacatcc tcttcccctc ctcccaggct ggggctcaca    2460
gacagccccc tggttggccc atccccagtg actgtgtgtt gatcaggcgc ccagtcacgc    2520
ggcctgctcc cctccaccca accccagggc tctatgggaa ggaccagcag gaggcagccc    2580
tggtggacat ggtgaatgac ggcgtggagg acctccgctg caaatacatc tccctcatct    2640
acaccaacta tgtgagcatc tgcaccaggg ttgggcactg ggggctgaac aaagaaaggg    2700
gcttcttgtg ccctcacccc ccttacccct caggtggctt gggctgaccc cttcttgggt    2760
cagggtgcag gggctgggtc agctctgggc caggggccca ggggcctggg acaagacaca    2820
acctgcaccc ttattgcctg gacatcaac cagccaagta acggtcatg ggggcgagtg     2880 caaggacaga gacctccagc aactggtggt ttctgatctc ctgggtggc gagggcttcc     2940 tggagtagcc agaggtggag gaggatttgt cgccagtttc tggatggagg tgctggcact   3000
tttagctgag gaaaatatgc agacacagag cacatttggg gacctgggac cagttcagca    3060
gaggcagcgt gtgtgcgcgt gcgtgtgcgt gtgtgtgcgt gtgtgtgtgt acgcttgcat   3120
ttgtgtcggg tgggtaagga gatagagatg ggcgggcagt aggcccaggt cccgaaggcc    3180
ttgaacccac tggtttggag tctcctaagg gcaatggggg ccattgagaa gtctgaacag    3240
ggctgtgtct gaatgtgagg tctagaagga tcctccagag aagccagctc taaagctttt    3300
gcaatcatct ggtgagagaa cccagcaagg atggacaggg agaatggaat agagatgagt    3360
tggcagctga agtggacagg atttggtact agcctggttg tggggagcaa gcagaggaga    3420
```

```
atctgggact ctggtgtctg gcctggggca gacggggtg tctcagggc tgggagggat      3480 gagagtagga tgatacatgg tggtgtctgg caggaggcgg gcaaggatga ctatgtgaag    3540
gcactgcccg ggcaactgaa gcctttgag accctgctgt cccagaacca gggaggcaag     3600
accttcattg tgggagacca ggtgagcatc tggccccatg ctgttccttc ctcgccaccc    3660
tctgcttcca gatggacaca ggtgtgagcc atttgtttag caaagcagag cagacctagg    3720
ggatgggctt aggccctctg cccccaattc ctccagcctg ctcccgctgg ctgagtccct    3780 agccccctg ccctgcagat ctccttcgct gactacaacc tgctggactt gctgctgatc     3840
catgaggtcc tagcccctgg ctgcctggat gcgttccccc tgctctcagc atatgtgggg    3900
cgcctcagtg cccggcccaa gctcaaggcc ttcctggcct cccctgagta cgtgaacctc    3960
cccatcaatg gcaacgggaa acagtgaggg ttgggggac tctgagcggg aggcagagtt     4020
tgccttcctt tctccaggac caataaaatt tctaagagag ctactatgag cactgtgttt    4080
cctgggacgg ggcttagggg ttctcagcct cgaggtcggt gggagggcag agcagaggac    4140
tagaaaacag ctcctccagc acagtcagtg gcttcctgga gccctcagcc tggctgtgtt    4200
tactgaacct cacaaactag aagaggaaga aaaaaaaga gagagagaaa caaagagaaa     4260
ta                                                                   4262
```